(12) United States Patent
Alphandery et al.

(10) Patent No.: US 9,359,589 B2
(45) Date of Patent: Jun. 7, 2016

(54) USE OF AT LEAST ONE CHELATING AGENT INTRODUCED INTO THE CULTURE MEDIUM OF MAGNETOTACTIC BACTERIA IN ORDER TO STIMULATE THE GROWTH THEREOF

(75) Inventors: Edouard Alphandery, Paris (FR); Iméne Chebbi, Epinay sur Seine (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/116,025

(22) PCT Filed: May 4, 2012

(86) PCT No.: PCT/IB2012/052235
§ 371 (c)(1),
(2), (4) Date: Dec. 23, 2013

(87) PCT Pub. No.: WO2012/153247
PCT Pub. Date: Nov. 15, 2012

(65) Prior Publication Data
US 2014/0106436 A1    Apr. 17, 2014

(30) Foreign Application Priority Data

May 6, 2011    (FR) ...................................... 11 53938

(51) Int. Cl.
| *C12N 1/38* | (2006.01) |
| *C12N 1/20* | (2006.01) |
| *C12N 1/00* | (2006.01) |
| *C12P 3/00* | (2006.01) |

(52) U.S. Cl.
CPC .. *C12N 1/20* (2013.01); *C12N 1/38* (2013.01); *C12P 3/00* (2013.01)

(58) Field of Classification Search
CPC ............... C12N 1/00; C12N 1/20; C12N 1/38
USPC ...................................... 435/243, 253.6, 244
See application file for complete search history.

(56) References Cited

U.S. PATENT DOCUMENTS

| 6,251,365 B1 | 6/2001 | Bauerlein et al. |
| 2003/0028071 A1 | 2/2003 | Handy et al. |
| 2006/0167313 A1 | 7/2006 | Naik et al. |
| 2008/0268061 A1 | 10/2008 | Jordan et al. |
| 2012/0302819 A1* | 11/2012 | Alphandery et al. ............. 600/9 |

FOREIGN PATENT DOCUMENTS

| CN | 101376900 A | 3/2009 |
| CN | 101434921 A | 5/2009 |
| CN | 101434922 A | 5/2009 |
| WO | WO 2004/064921 A1 | 8/2004 |
| WO | WO 2011/061259 A1 | 5/2011 |

OTHER PUBLICATIONS

Wolin et al. Formulation of Methane by Bacterial Extracts; The Journal of Biological Chemistry, vol. 238, No. 8 (1963) pp. 2882-2886.*
Blakemore et al. Isolation and Pure Culture of a Freshwater Magnetic Spirillum in Chemically Defined Medium; Journal of Bacteriology, vol. 140, No. 2 (1979) pp. 720-729.*
Taoka et al. Identification of Iron Transporters Expressed in the Magnetotactic Bacterium Magnetospiirillum Magnetotactium; Current Microbiology, vol. 58, No. 2 (2009) pp. 177-188.*
Bazylinski et al., "Magnetosome Formation in Prokaryotes," *Nature Reviews/Microbiology*, Mar. 2004, vol. 2, pp. 217-230.
Arakaki et al., "Formation of Magnetite by Bacteria and its Application," *Journal of the Royal Society Interface*, Jun. 17, 2008, vol. 5, pp. 977-999.
Sun et al., "In Vitro and In Vivo Antitumor Effects of Doxorubicin Loaded with Bacterial Magnetosomes (DBMs) on H22 Cells: The Magnetic Bio-Nanoparticles as Drug Carriers," *Cancer Letters*, Aug. 2007, vol. 258, pp. 109-117.
Sun et al., "Targeted Distribution of Bacterial Magnetosomes Isolated from *Magnetospirillum Gryphiswaldense* MSR-1 in Healthy Sprague-Dawley Rats," *Journal of Nanoscience and Nanotechnology*, 2009, vol. 9, pp. 1881-1885.
Sun et al., "Biocompatibility of Bacterial Magnetosomes: Acute Toxicity, Immunotoxicity and Cytotoxicity," *Nanotoxicology*, Sep. 2010, vol. 4, No. 3, pp. 271-283.
Alphandery et al., "Heat Production by Bacterial Magnetosomes Exposed to an Oscillating Magnetic Field," *J. Phys. Chem. C*, Dec. 13, 2010, vol. 115, pp. 18-22.
Heyen et al., "Growth and Magnetosome Formation by Microaerophilic *Magnetospirillum* Strains in an Oxygen-Controlled Fermentor," *Appl. Microbiol Boitechnol*, 2003, vol. 61, pp. 536-544.
Lang et al., "Biogenic Nanoparticles: Production, Characterization, and Application of Bacetrial Magnetosomes," *Journal of Physics: Condensed Matter*, 2006, vol. 18, pp. S2815-S2828.
Widler et al., "Highly Potent Geminal Bisphosphonates. From Pamidronate Disodium (Aredia) to Zoledronic Acid (Zometa)," *J. Med. Chem.*, Jul. 19, 2002, vol. 45, pp. 3721-3738.
Neves et al., "Synthesis, Characterization and Biodistribution of Bisphosphonates Sm-153 Complexes: Correlation with Molecular Modeling Interaction Studies," *Nuclear Medicine and Biology*, 2002, vol. 29, pp. 329-338.
Shinoda et al., "Structure-Activity Relationships of Various Bisphosphonates," *Calcif Tissue Int*, 1983, vol. 35, pp. 87-99.
Merrell et al., "Inhibition of the Mevalonate Pathway and Activation of p38 MAP Kinase are Independently Regulated by Nitrogen-Containing Bisphosphonates in Breast Cancer Cells," *European Journal of Pharmacology*, Jun. 16, 2007, vol. 570, pp. 27-37.
Kundu et al., "Enhancement of Magnetotactic Bacterial Yield in a Modified MSGM Medium without Alteration of Magnetosomes Properties," *Indian Journal of Experimental Biology*, May 2010, pp. 518-523.

(Continued)

Primary Examiner — Kagnew H Gebreyesus
Assistant Examiner — Paul Martin
(74) *Attorney, Agent, or Firm* — Oliff PLC

(57) ABSTRACT

The invention relates to the use of at least one chelating agent, including an iron chelating agent, in order to stimulate the growth of magnetotactic bacteria.

5 Claims, 22 Drawing Sheets

(56) References Cited

OTHER PUBLICATIONS

Matsunaga et al., "Mass Culture of Magnetic Bacteria and their Application to Flow Type Immunoassays," *IEEE Transactions of Magnetics*, Sep. 1990, vol. 26, No. 5, pp. 1557-1559.

Yang et al., "Effects of Growth Medium Composition, Iron Sources and Atmospheric Oxygen Concentrations on Production of Luciferase-Bacterial Magnetic Particle Complex by a Recombinant *Magnetospirillum Magneticum* AMB-1," *Enzyme and Microbial Technology*, 2001, vol. 29, pp. 13-19.

Alphandery et al., "Chains of Magnetosomes Extracted from AMB-1 Magnetotactic Bacteria for Application in Alternative Magnetic Field Cancer Therapy," *ACS Nano*, 2011, vol. 5, No. 8, pp. 6279-6296.

International Search Report issued in International Patent Application No. PCT/IB2012/052235 dated Aug. 24, 2012 (with translation).

French Written Opinion issued in French Application No. 1153938 dated Dec. 2, 2011 (with translation).

\* cited by examiner ively used for magnetic hyperthermia (PCT No. WO 2004/064921 and American patent applications No. US 2003/0028071, No. US 2006/0167313 and No. US 2008/0268061). The experimental results already obtained indicate that magnetosome chains are good candidates for magnetic hyperthermia.

USE OF AT LEAST ONE CHELATING AGENT INTRODUCED INTO THE CULTURE MEDIUM OF MAGNETOTACTIC BACTERIA IN ORDER TO STIMULATE THE GROWTH THEREOF

FIELD OF THE INVENTION

The present invention relates to the obtaining of bacterial magnetosomes, mainly in the form of magnetosome chains extracted from magnetotactic bacteria after culturing these bacteria. More particularly, the invention relates to the use of specific additives, preferentially iron-chelating agents, which are introduced into the culture medium of magnetotactic bacteria and make it possible to simulate the growth thereof. The result of this is to increase their production yield over time. These magnetosome chains may, for example, be used in the cancer therapy field or in the cancer diagnosis field.

PRIOR ART

Magnetosomes are single-domain nanocrystals covered with a phospholipid membrane, which are composed of magnetite or greigite. Magnetosomes can become oxidized following their extraction from bacteria, changing from a composition of magnetite to a composition of maghemite. Magnetosomes are usually organized in the form of chains in bacteria. Magnetotactic bacteria use these magnetosome chains as a compass for navigating in the direction of Earth's magnetic field, which allows them to find the optimal conditions required for their survival and their development (Bazylinski et al., Nat. Rev. Microbiol. 2004, 2, 217-230). It has been shown that magnetosomes can be of use for a large number of applications, both in scientific fields and in commercial or medical fields. For example, they can be used for detecting individual nucleotide polymorphisms, for extracting DNA, or for magnetically detecting biomolecular interactions. They can also be used in immunological or receptor-binding assays or for separating cells (Arakaki et al., J. R. Soc. Interface, 2005, 5, 977-999). It has been suggested that bacterial magnetosomes can be inserted into liposomes for drug delivery (U.S. Pat. No. 6,251,365 B1). The antitumor activity of a complex made up of bacterial magnetosomes and of doxorubicin has also been shown experimentally (Sun et al., Cancer. Lett., 2007, 258, 109-117).

Furthermore, recent studies appear to indicate that magnetosomes are not very toxic, which makes them good candidates for medical applications (Sun et al., J. Nanosci. Nanotechnol., 2009, 9, 1881-1885, Sun et al., Nanotoxicology, 2010, 4, 271-283).

In the field of application on which the inventors work, i.e. magnetic hyperthermia, it has been shown that magnetosomes are highly effective. Magnetic hyperthermia is a technique generally used for treating cancer (solid tumors) according to which magnetic nanoparticles are sent or administered into tumors and then heated under the application of an alternative magnetic field. The heat given off by the nanoparticles produces the antitumor effect, destruction of the tumor cells. Owing to their considerable heating capacity (which is due essentially to their large size) and to their arrangement in chains, magnetosomes have been shown by the inventors to be particularly effective for magnetic hyperthermia (Alphandéry et al., J. Phys. Chem. C, 2011, 115, 18-22, patent PCT/EP2010/067765). The inventors have also shown, in patent PCT/EP2010/067765, that magnetosome chains are more effective than the superparamagnetic iron oxide nanoparticles (SPIONs) which are currently used for magnetic hyperthermia (PCT No. WO 2004/064921 and American patent applications No. US 2003/0028071, No. US 2006/0167313 and No. US 2008/0268061). The experimental results already obtained indicate that magnetosome chains are good candidates for magnetic hyperthermia.

Magnetosomes can therefore be used for numerous applications given their properties which are advantageous or different than those of chemically synthesized nanoparticles (SPIONs). However, the low production yield of magnetotactic bacteria is a difficulty that remains to be overcome in order to enable easy marketing for these magnetosomes. Efforts have been undertaken to improve the production yield of magnetotactic bacteria, in particular by proposing culturing the magnetotactic bacteria under controlled conditions (U. Heyen et al., Appl. Microbiol. Biotechnol., 2003, 61, 536-544, C. Lang et al., J. Phys. Condens. Matter., 2006, 18, S2815-S2828, Chinese patents CN 101376900 (A), CN 101434922 (A) and CN 101434921 (A)).

SUMMARY OF THE INVENTION

The inventors have sought to develop methods for producing magnetosomes with an improved yield.

In this context, the present invention proposes to use varied additives for stimulating the growth of magnetotactic bacteria, the result of which is to increase the production yield of the magnetotactic bacteria over time.

The method proposed according to the invention can be combined with methods already known in the prior art in order to even further improve the production yield of magnetotactic bacteria, some of which methods have been mentioned above.

The present invention relates to the use of at least one chelating agent, including an iron-chelating agent, for stimulating the growth of magnetotactic bacteria.

In certain embodiments, the chelating agents are chosen in particular from (i) chelating agents which have one or more carboxyl groups, (ii) chelating agents which have one or more hydroxyl groups, (iii) chelating agents which have one or more amino and/or carboxyl and/or ketone groups, (iv) chelating agents which have one or more phosphonate and/or phosphonic acid groups, (v) chelating agents which have one or more bisphosphonate and/or trisphosphonate and/or tetraphosphonate groups, (vi) chelating agents which have one or more sulfonate and/or sulfonic acid groups, and (vii) chelating agents of polydentate type, of polymeric type, for example of polysaccharide type.

In certain embodiments, said chelating agent is chosen from rhodamine B, ascorbic acid, citric acid, hemoglobin, a 1000 Da dextran, anthranilic acid, calcein, alendronate, 3-[cyclohexylamino]-1-propanesulfonic acid (CAPS) and EDTA.

DESCRIPTION OF THE FIGURES

FIG. 1 illustrates the effect of hemoglobin, of EDTA, of anthranilic acid, of citric acid, of 3-(N-morpholino)propanesulfonic acid and of 3-[cyclohexylamino]-1-propanesulfonic acid on the growth of magnetotactic bacteria and on the production of magnetosomes after 7 days of culture. This study was carried out on 1 liter of culture medium.

FIG. 2 illustrates the effect of neridronate, alendronate, nicotinamide, dextran, calcein and rhodamine B on the growth of magnetotactic bacteria and on the production of magnetosomes after 7 days of culture. This study was carried out on 1 liter of culture medium.

FIG. 4 illustrates the effect of the presence of rhodamine B in the culture medium of magnetotactic bacteria on bacterial proliferation and on magnetosome production.

FIG. 6 illustrates the effect of the presence of ascorbic acid in the culture medium of magnetotactic bacteria on bacterial proliferation and on magnetosome production.

DETAILED DESCRIPTION OF THE INVENTION

Figure 1A:
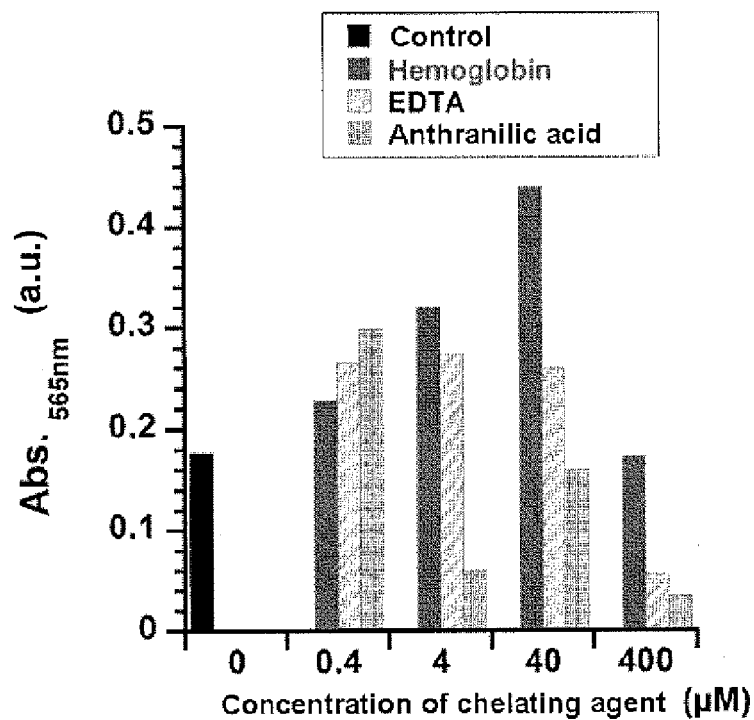
FIG. 1A represents, in histogram form, the absorption (measured at 565 nm) as a function of the concentration of hemoglobin, EDTA and anthranilic acid. Along the y-axis: absorbance, expressed in arbitrary units (a.u.). Along the x-axis: concentration of chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: hemoglobin, EDTA and anthranilic acid.
Figure 1B:
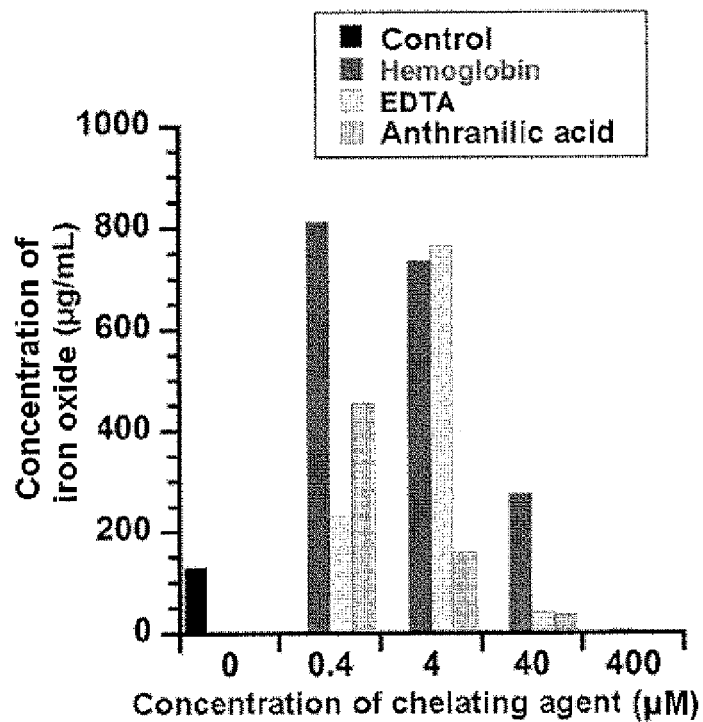
FIG. 1B represents, in histogram faun, the concentration of iron oxide (measured by absorption at 480 nm) as a function of the concentration of hemoglobin, EDTA and anthranilic acid. Along the y-axis: concentration of iron oxide, expressed in µg/ml. Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: hemoglobin, EDTA and anthranilic acid.
Figure 1C:
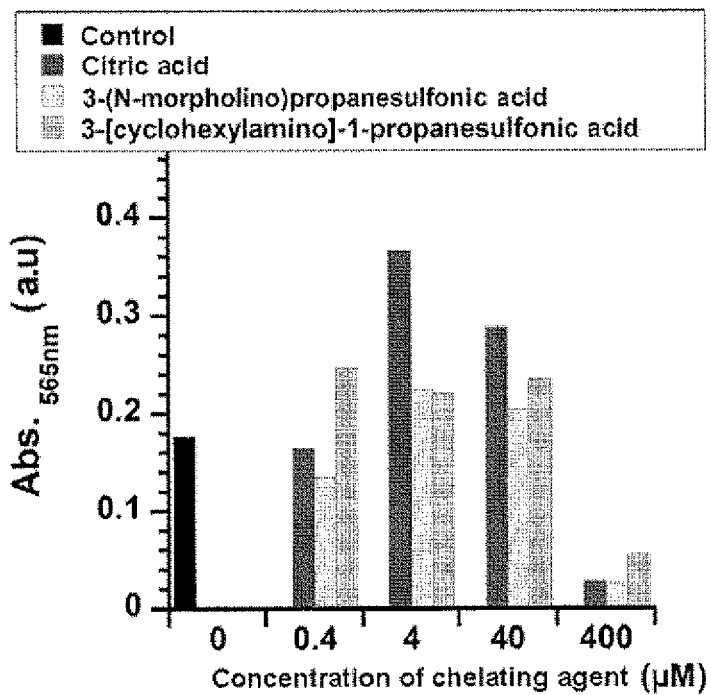
FIG. 1C represents, in histogram form, the absorption (measured at 565 nm) as a function of the concentration of citric acid, 3-(N-morpholino)propanesulfonic acid and 3-[cyclohexylamino]-1-propanesulfonic acid. Along the y-axis: absorbance, expressed in arbitrary units (a.u.). Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: citric acid, 3-(N-morpholino)propanesulfonic acid and 3-[cyclohexylamino]-1-propanesulfonic acid.
Figure 1D:
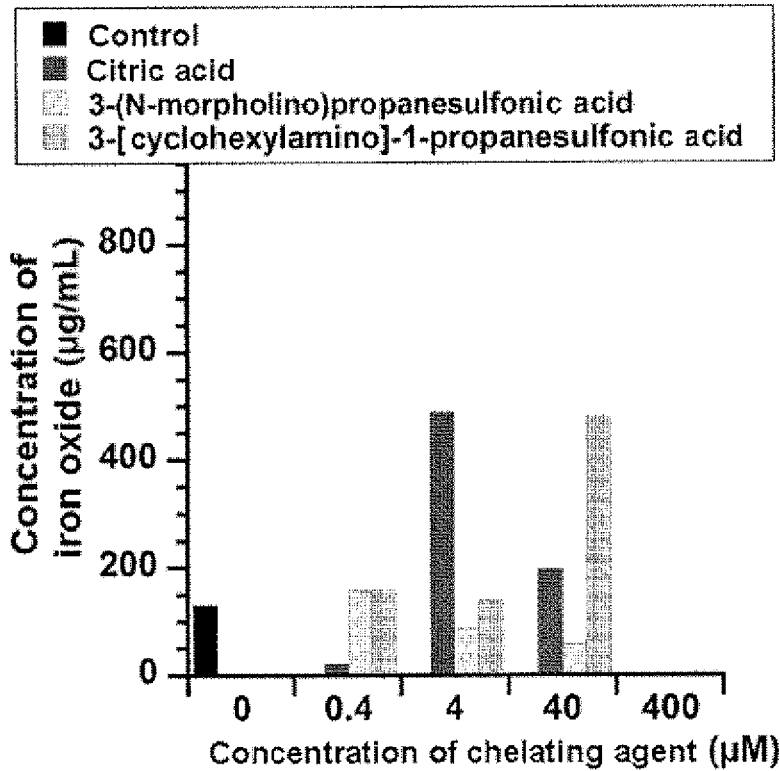
FIG. 1D represents, in histogram form, the concentration of iron oxide (measured by absorption at 480 nm) as a function of the concentration of citric acid, 3-(N-morpholino)propanesulfonic acid and 3-[cyclohexylamino]-1-propanesulfonic acid. Along the y-axis: concentration of iron oxide, expressed in µg/ml. Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: citric acid, 3-(N-morpholino)propanesulfonic acid and 3-[cyclohexylamino]-1-propanesulfonic acid.
Figure 2A:
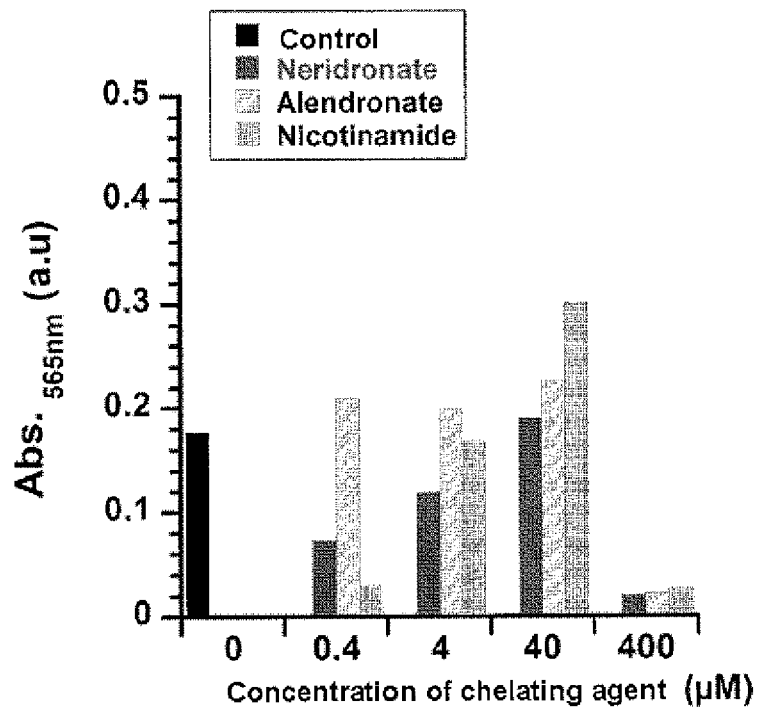
FIG. 2A represents, in histogram form, the absorption (measured at 565 nm) as a function of the concentration of Neridronate, Alendronate and Nicotinamide. Along the y-axis: absorbance, expressed in arbitrary units (a.u,). Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: neridronate, alendronate and nicotinamide.
Figure 2B:
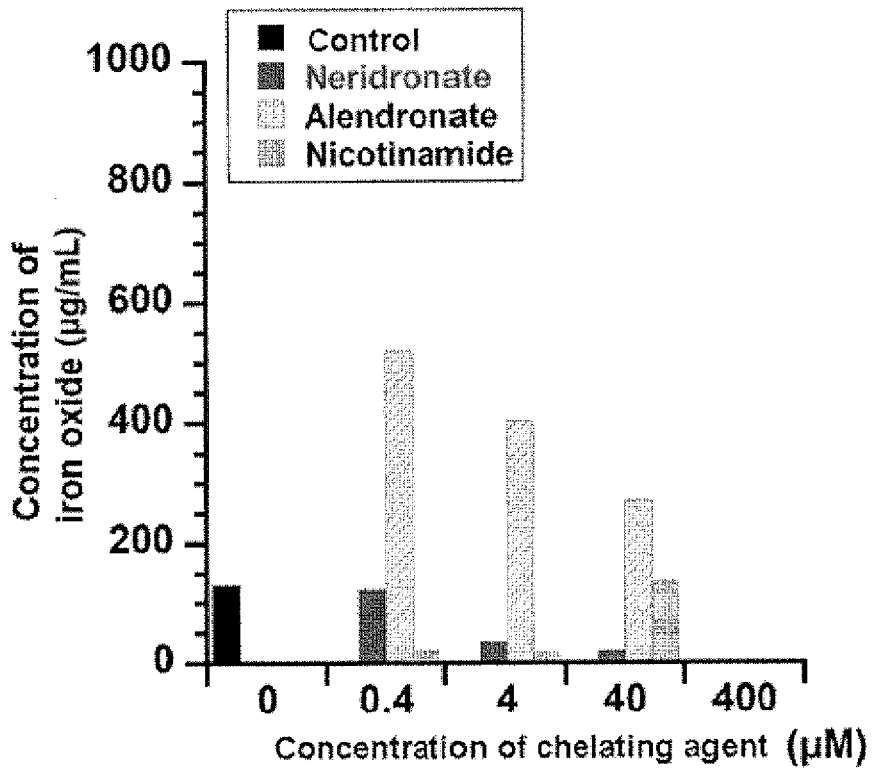
FIG. 2B represents, in histogram form, the concentration of iron oxide (measured by absorption at 480 nm) as a function of the concentration of Neridronate, Alendronate and Nicotinamide. Along the y-axis: concentration of iron oxide, expressed in µg/ml. Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: neridronate, alendronate and nicotinamide.
Figure 2C:
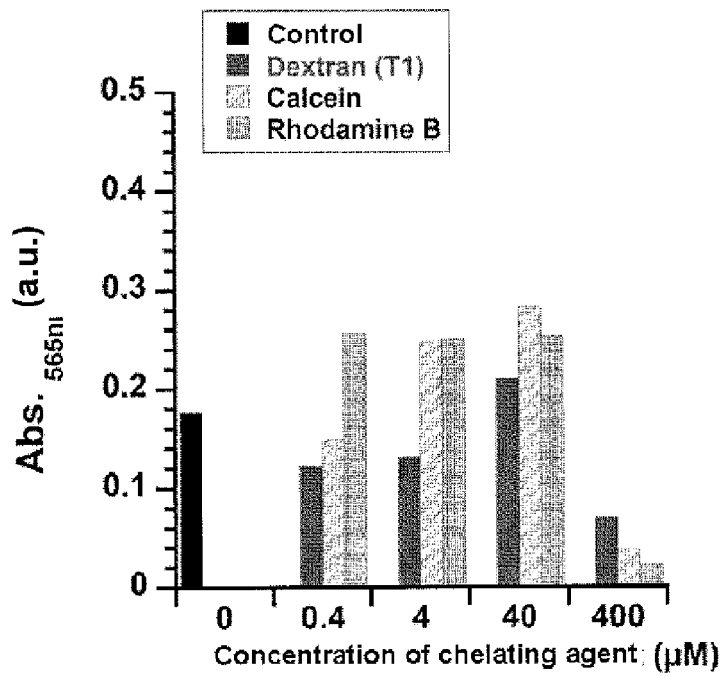
FIG. 2C represents, in histogram form, the absorption (measured at 565 nm) as a function of the concentration of dextran (T1), calcein and rhodamine B. Along the y-axis: absorbance, expressed in arbitrary units (a.u.). Along the x-axis: concentration of the chelating agent. From left to right of the figure: the control in the absence of chelating agent, then in the presence of the chelating agent at increasing concentrations of 0.4 µM, 4 µM, 40 µM and 400 µM, From left to right, for each concentration of chelating agent: dextran (T1), calcein and rhodamine.
Figure 2D:
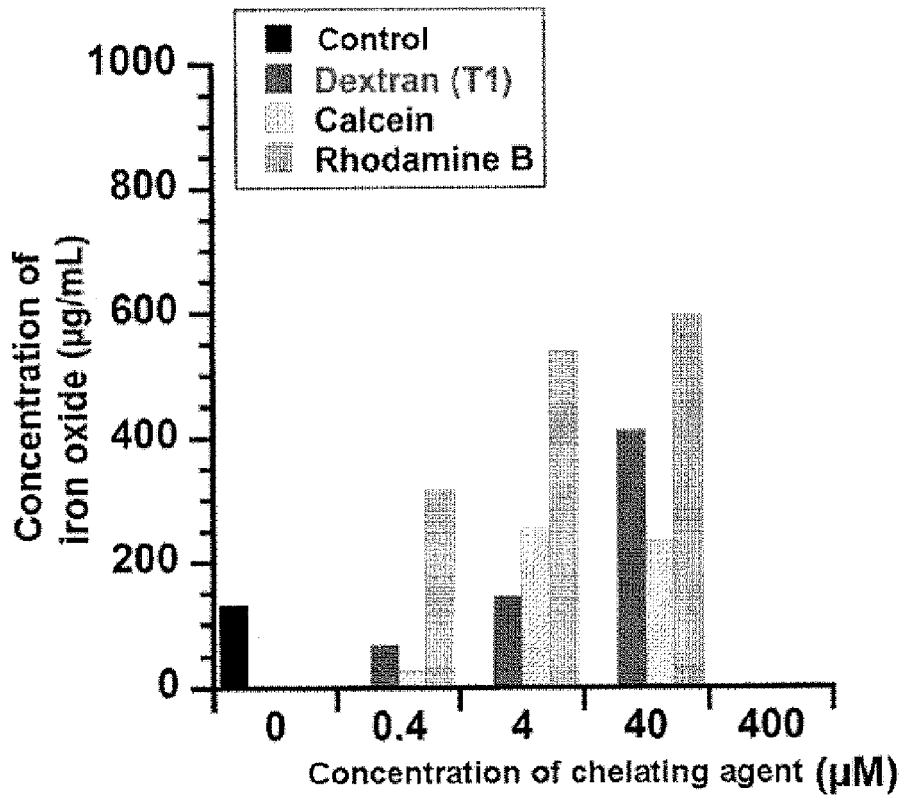
FIG. 2D represents, in histogram form, the concentration of iron oxide (measured by absorption at 480 nm) as a function of the concentration of Dextran, Calcein and Rhodamine B. Along the y-axis: concentration of iron oxide, expressed in µg/ml. Along the x-axis: concentration of the chelating agent. From left to right of the figure: the control in the absence of chelating agent, then in the presence of the chelating agent at increasing concentrations of 0.4 µM, 4 µM, 40 µM and 400 µM. From left to right, for each concentration of chelating agent: dextran (T1), calcein and rhodamine.

Novel methods for obtaining bacterial magnetosome chains are provided according to the invention.

It has been shown, according to the invention, that culturing magnetotactic bacteria in the presence of at least one chelating agent, in particular of at least one iron-chelating agent, significantly stimulates the growth of said bacteria and thus makes it possible to obtain an increased amount of bacterial cells after a given culture time.

The effect of stimulating the growth of magnetotactic bacteria has been shown in the examples with a large variety of chelating agents, in particular with a large variety of iron-chelating agents, such as:

a chelating agent comprising one or more carboxyl groups, such as EDTA, rhodamine B, ascorbic acid, anthranilic acid, calcein, erythrosine or 3-[cyclohexylamino]-1-propanesulfonic acid (CAPS), a chelating agent comprising one or more groups of phosphonate type, including bisphosphonate, trisphosphonate or tetraphosphonate type, such as alendronate and neridronate, a polymeric chelating agent, such as a low-molecular-weight dextran (molecular weight ranging from 500 Da to 2000 Da, for instance dextran T1), or a low-molecular-weight carboxymethyl dextran (molecular weight ranging from 500 Da to 2000 Da), and a chelating agent of polydentate type, such as hemoglobin.

The present invention relates to the use of at least one chelating agent, preferably of at least one iron-chelating agent, for stimulating the growth of magnetotactic bacteria.

As emerges from the data which appear hereinafter, a stimulation of the growth of magnetotactic bacteria is to be distinguished from an increase in the production of magnetosomes by these same bacteria, which may be jointly observed. Stimulation of the growth of the bacteria is reflected first and foremost by an acceleration of the process of maturation of these bacteria.

All of the results obtained by the applicant show that the use of a chelating agent, or of a combination of chelating agents, in a culture of magnetotactic bacteria, makes it possible to obtain a bacterial biomass comprising magnetosome chains either (i) more rapidly than when said magnetotactic bacteria are cultured in the absence of said chelating agent(s), or (ii) in greater amount than when said magnetotactic bacteria are cultured in the absence of said chelating agent(s), or (iii) more rapidly and in greater amount than when said magnetotactic bacteria are cultured in the absence of said chelating agent(s).

The term "magnetotactic bacterium" is intended to mean, according to the invention, a bacterium which synthesizes magnetosomes which are generally arranged in chains, as is described in the prior art. The specificity of these bacteria is that they use these magnetosome chains as a compass for navigating in the direction of Earth's magnetic field. The invention relates to this type of bacterium. The magnetotactic bacteria encompass *Magnetospirillum magneticum* (for example the AMB-1 and MS-1 strains, and the facultative anaerobic MGT-1 strain), the *Magnetococcus* MC-1 strain, the facultative anaerobic *Vibrio* strains MV-1, MV-2 and MV-4, *Magnetospirillum gryphiswaldense* (for example, the MSR-1 strain), and also *Desulfovibrio magneticus* (for example, the RS-1 strain). Other bacterial strains which can be likened to magnetotactic bacteria are also encompassed by the invention.

The term "chelating agent" is intended to mean, according to the invention, an agent capable of complexing at least one transition metal preferentially chosen from iron, copper, zinc, manganese, cobalt and nickel. The chelating agents which are preferred according to the invention are iron-chelating agents.

The growth of bacteria in an unrenewed culture medium generally comprises several phases, respectively (i) a lag phase, (ii) an acceleration phase, (iii) an exponential phase, (iv) a deceleration phase and (v) a stationary phase. During the lag phase (i), the bacteria usually synthesize the enzymes that they will require in order to use the substrates. During the acceleration phase (ii), bacterial divisions begin. During the exponential phase (iii), the bacterial cell multiplication rate is at a maximum. During the deceleration phase (iv), the bacterial cell multiplication rate decreases, owing in particular to the increasing depletion of resources in terms of nutrients. Finally, during the stationary phase (v), the multiplication rate becomes zero, with as many cells being created as there are cells which die. It may be added that, if the culturing is continued, the stationary phase is followed by a phase of decline in which the cells die without being renewed, owing to the lack of nutrients.

The term "stimulation of the growth" of magnetotactic bacteria is intended to mean an increase in the rate at which bacteria multiply or in the amount of magnetotactic bacteria produced. This stimulation can be initiated during any phase of bacterial growth. It occurs more particularly during the exponential phase. Thus, for a culture of magnetotactic bacteria prepared in the presence of a chelating agent, or of a combination of chelating agents, said culture being in any of phases (i) to (v), more particularly in the exponential growth phase, a stimulation of bacterial growth is measured either (i) when the amount of bacteria cultured in the presence of chelating agent(s) is greater than the amount of bacteria of a culture which is identical but prepared in the absence of said chelating agent, or of said combination of chelating agents, or (ii) when the increase, measured over time, in the number of bacteria cultured in the presence of chelating agent(s) is more rapid than the increase, measured over time, in the number of bacteria of a culture which is identical but prepared in the absence of said chelating agent, or of said combination of chelating agents.

The amount of bacteria present in suspension in a culture medium is proportional to the value of the absorption of this suspension. The higher the absorption, the higher the number of bacteria present in the suspension. It is thus common practice to measure the variation in the number of bacteria as a function of the day of growth, which is referred to as a growth curve, by spectrophotometry, by measuring the absorbance at at least one given wavelength as a function of the day of growth (U. Heyen, *Appl. Microbiol. Biotechnol.* 2003, 61, 536-544). In certain embodiments, the absorbance is measured at a plurality of wavelengths, including at two given wavelengths. A spectrum ranging from the near ultraviolet to the near infrared was produced, namely from 300 nanometers to 600 nanometers, with a scan rate of 100 nm/min and a measurement interval of 0.5 nm between each absorbance measurement. In certain embodiments, for example when using a chelating agent which absorbs light at the measurement wavelength, the absorbance measurement can be carried out at at least one other wavelength at which said chelating agent does not absorb light. However, in most cases, the small amount of chelating agent which is added in order to stimulate the growth of the magnetotactic bacteria does not cause any substantial change in the light absorption properties of the cell suspension, at the measurement wavelength.

For the purposes of the invention, the growth of the magnetotactic bacteria is stimulated when the culture studied has an absorbance value which is at least 5% higher, compared with a control culture. Generally, the absorbance is conventionally expressed as optical density (O.D.) value, as is in particular illustrated in the examples.

An O.D. value which is at least 5% higher compared with a control encompasses O.D. values which are at least 10%, 15%, 20%, 25%, 30%, 35%, 40%, 45%, 50%, 55%, 60%, 65%, 70%, 75%, 80%, 90%, 95%, or at least 100%, higher, compared with said control.

According to the invention, the stimulation of the growth of the magnetotactic bacteria in the presence of one or more chelating agents introduced into the culture medium is generally accompanied by an increase in the amount of magnetosomes produced. The production of magnetosomes in greater amount, in the presence of a chelating agent can result from the effect of stimulation of the growth of the magnetotactic bacteria which was identified according to the invention. The production of magnetosomes in greater amount, can also result from increased production of magnetosomes by each bacterial cell or else from an increased percentage of bacterial cells producing magnetosomes. The increased production of magnetosomes can also result from a combination of the abovementioned mechanisms.

The use of a chelating agent, or of a combination of chelating agents, in a method for culturing magnetotactic bacteria also makes it possible, for a given number of bacteria in a starting culture, to more rapidly obtain a given amount of bacteria. In other words, the use of at least one chelating agent for culturing magnetotactic bacteria results in the production of magnetotactic bacteria with an increased yield compared to the known methods carried out without chelating agent.

Generally, the chelating agents are chosen in particular from (i) chelating agents which have one or more carboxyl groups, (ii) chelating agents which have one or more hydroxyl groups, (iii) chelating agents which have one or more amino and/or carboxyl and/or ketone groups, (iv) chelating agents which have one or more phosphonate and/or phosphonic acid groups, (v) chelating agents which have one or more bisphosphonate and/or trisphosphonate and/or tetraphosphonate groups, (vi) chelating agents which have one or more sulfate and/or sulfonic acid groups, and (vii) chelating agents of polydentate types and/or polymeric types, for example of polysaccharidique type.

It is specified that a particular chelating agent may comprise a plurality of functional groups, for example among carboxyl, hydroxyl or amino groups, and thus be classified in absolute manner in more than one category, among the abovementioned categories (i) to (vii). However, the various chelating agents may be classified according to the type of main functional group which characterizes them, as specified hereinafter.

In certain embodiments, the chelating agents are chosen from agents which have one or more carboxyl groups, such as ALA (alpha-lipoic acid), calcein, carboxyfluorescein, deferasirox, dipicolinic acid, DTPA (diethylenetriaminepentaacetic acid), EDTA (ethylenediaminetetraacetic acid), folic acid (vitamin B9), lactic acid, rhodamine B, a carboxymethyl dextran, oxalic acid, citric acid, a compound comprising one or more citric and/or citrate functional groups, and phenolic acid. A chelating agent within the meaning of the invention may also be a compound comprising one or more acetate and/or acetic functional groups encompassing BAPTA (aminophenoxyethanetetraacetic acid), CDTA (cyclohexane-1,2-diaminetetraacetic acid), EDDHMA (ethylenediamined(o-hydroxy-p-methylphenyl)acetic acid), $CaNa_2$-EDTA, EDTCA (ethylenediaminetetraacetic acid with Cetavlon® (ammonium-type surfactant)), EDDA (ethylenediamine-N,N'-diacetic acid), EDDHA (ethylenediamine-N,N'-bis(2-hydroxyphenylacetic acid), EGTA (ethylene glycol bis(β-aminoethyl ether)-N,N,N',N'-tetraacetic acid), HEDTA (N-(2-hydroxyethyl)ethylenediaminetriacetic acid), HEEDTA (hydroxy-2-ethylenediaminetriacetic acid) and NTA (nitrilo triacetate).

In other embodiments, the chelating agent is a molecule comprising one or more hydroxyl functional groups, such as catechol or derivatives thereof, or else deferiprone.

In other embodiments, the chelating agent is a molecule comprising one or more amino functional groups, such as dopamine and/or deferoxamine.

In other embodiments, the chelating agent is a molecule comprising one or more aminocarboxylic and/or ketone functional groups, such as doxorubicin, caffeine, D-penicillamine, pyrroloquinoline and HEIDA (hydroxyethylimino-N,N-diethanoic acid).

In certain embodiments, the chelating agent is a molecule comprising at least one phosphonate or phosphonic functional group, such as AEPN (2-aminoethylphosphonic acid), AMP (aminotris(methylenephosphonate)), ATMP (aminotris (methylenephosphonic acid)), CEPA (2-carboxyethylphosphonic acid), DMMP (dimethyl methylphosphonate), DTPMP (diethylenetriaminepenta(methylenephosphonic acid)), EDTMP (ethylenediaminetetra(methylenephosphonic acid)), HEDP (1-hydroxyethylidene-1,1-diphosphonic acid), HDTMP (hexamethylenediaminetetra(methylenephosphonic acid)), HPAA (2-hydroxyphosphonocarboxylic acid), PBTC (phosphonobutanetricarboxylic acid), PMIDA (N-(phosphonomethyl)iminodiacetic acid), TDTMP (tetramethylenediamine-tetra(methylenephosphonic acid)), ADP (adenosinediphosphoric acid) or 1-{12-[4-(dipyrromethene boron difluoride)butanoyl]amino}dodecanoyl-2-hydroxy-sn-glycero-3-phosphate, a sodium salt of L-α-phosphatidic acid, and a sodium salt of 1-palmitoyl-2-(dipyrromethene boron difluoride)undecanoyl-sn-glycero-3-phospho-L-serine.

In certain embodiments, the chelating agent is a molecule containing at least one bisphosphonate, trisphosphonate or tetraphosphonate functional group, such as 1-hydroxymethylene-bis-phosphonic acid, propanetriphosphonic acid, (nitrilotris(methylene))trisphosphonic acid or (phosphinylidynetris(methylene))trisphosphonic acid. The 1-hydroxymethylene-bis-phosphonic acids encompass alendronic acid (sold under the name fosamax®), pamidronic acid, zoledronic acid, risedronic acid, neridronic acid, ibandronic acid (sold under the name bondronat®), minodronic acid and other compounds described in the prior art (see, for example, L. Wilder et al., *J. Med. Chem.,* 2002, 45, 3721-3728; M. Neves, N. Med. Biol., 2002, 29, 329-338; H. Shinoda et al., Calcif. Tissue Int., 1983, 35, 87-89; M. A. Merrell, Eur. J. Pharmacol., 2007, 570, 27-37).

In certain embodiments, the chelating agent is a molecule comprising one or more sulfonate or sulfonic acid functional groups, or else a dimercapto group, such as BPDS (bathophenanthroline disulfonate or 4,7-di(4-phenylsulfonate)-1,10-phenanthroline), DMPS (dimercaptopropane sulfonate or 2,3-dimercapto-1-propanesulfonic acid), sulforhodamine 101, and DMSA (dimercaptosuccinic acid).

Other examples of chelating agents encompass polydentate ligands, i.e. chelating agents having more than one atom capable of binding to a metal atom, such as hemoglobin, chlorophyll, porphyrins and organic compounds containing pyrrole rings.

Other examples of chelating agents encompass polymeric compounds, in particular polysaccharide compounds.

Thus, in certain embodiments, a chelating agent is chosen from rhodamine B, ascorbic acid, citric acid, folic acid, erythrosine, hemoglobin, a low-molecular-weight dextran, anthranilic acid, calcein, alendronate, 3-[cyclohexylamino]-1-propanesulfonic acid (CAPS) and EDTA. For the purpose of the invention, a low-molecular-weight dextran is a dextran having a molecular weight of less than 2000 Da, and preferentially less than 1000 Da. A low-molecular-weight dextran has a molecular weight greater than 100 Da, and preferentially greater than 500 Da.

In certain embodiments, the chelating agent is chosen from compounds having an anticancer activity. Such a chelating agent may, for example, be temozolomide or certain bisphosphonate compounds.

The chelating agent(s) is (are) advantageously used in a culture medium for magnetotactic bacteria at a final concentration ranging from 0.02 μM to 1 mM.

In certain embodiments, the chelating agent(s) is (are) advantageously used in a culture medium for magnetotactic bacteria at a final concentration ranging from 0.02 μM to 500 μM.

In certain embodiments, the chelating agent(s) is (are) advantageously used in a culture medium for magnetotactic bacteria at a final concentration ranging from 0.1 μM to 200 μM.

The examples illustrate that the optimum final concentration of each chelating agent in the culture medium for magnetotactic bacteria can vary according to the chelating agent which is selected. However, for each of the chelating agents, the optimum final concentration for use in a culture of magnetotactic bacteria is easily determined by those skilled in the art, by simple routine tests using the culture conditions described in the examples.

The results of the examples show that the various chelating agents tested can be used at a final concentration ranging from 0.04 μM to 40 μM.

Advantageously, the magnetotactic bacteria of interest are placed in culture in a medium comprising at least one iron source, such as an iron quinate solution, and comprising additives such as transition metals other than iron, and a chelating agent or a combination of chelating agents. By way of illustration, the magnetotactic bacteria can be placed in culture in MSGM medium, as described, for example, by Kundu et al. (2010, Indian J Exp Biol, Vol. 48: 518-523) or else in the examples hereinafter.

In certain embodiments, the chelating agent(s) is (are) used to complex iron in the form of both $iron^{2+}$ and $iron^{3+}$ in the molar ratio of 1 to 2 of magnetite, which allows optimization of magnetosome magnetite synthesis.

In certain embodiments, the chelating agent(s) is (are) used at pH values different than the optimum published for culturing strains of magnetotactic bacteria, which allows optimization of magnetosome magnetite synthesis.

Generally, a method for culturing magnetotactic bacteria in accordance with the invention comprises the following steps:
a) adding magnetotactic bacteria to an appropriate culture medium containing a chelating agent or a combination of chelating agents,
b) culturing the magnetotactic bacteria in said medium, under chosen operating conditions,
c) recovering the magnetotactic bacterial cells obtained at the end of step b).

Generally, step b) is carried out at ambient temperature, i.e. at approximately 25° C.

Generally, step b) is continued until at least the exponential growth phase of the magnetotactic bacteria is reached. In certain embodiments, step b) is continued until the stationary growth phase of the magnetotactic bacteria is reached.

In certain embodiments, the duration of step b) ranges from 1 to 15 days following inoculation of the bacteria into the culture medium. The duration of step b) is advantageously from 2 to 9 days, and preferentially from 2 to 6 days.

Then, in step c), the recovering of the magnetotactic bacteria can be carried out conventionally, for example by centrifuging the suspension of bacterial cells, and then recovering the pellet containing the magnetotactic bacteria.

In preferred embodiments, the method for culturing magnetotactic bacteria described above consists of a continuous culturing method.

The continuous culturing method can be carried out by means of any known type of continuous cell culture device.

By way of illustration, those skilled in the art can use a Biostat®Aplus device sold by the company Sartorius (France).

Typically, such a device comprises:

(I) a culture chamber which is temperature-regulated, pH-regulated and oxygen pressure-regulated, (II) a means for introducing, preferentially continuously, sterile culture medium and/or bacteria into the culture chamber, (III) a means for recovering, preferentially continuously, the culture medium and/or all or part of the bacteria cultured in the culture chamber.

Preferentially, the culture chamber (I) also comprises one or more of the following means:

(1) a means for regulating the temperature of the bacterial suspension present inside the chamber. Such a means may consist of a heat exchanger placed on the external wall of the culture chamber, such as a water circulation exchanger;

(2) a device for stirring the bacterial cell suspension contained in the culture chamber;

(3) one or more probes for measuring physical and/or chemical parameters of the culture conditions, which encompasses (a) probes for measuring the gases dissolved in the bacterial cell suspension medium, such as a probe for measuring the dissolved oxygen and/or a probe for measuring the dissolved nitrogen, (b) a probe for measuring pH, or else (c) a probe for measuring the temperature.

In certain embodiments of a culture method carried out continuously, (a) the culture chamber is fed with fresh sterile culture medium, (b) said culture medium is inoculated with the desired starting amount of magnetotactic bacteria, (c) said bacteria are cultured for a period of time sufficient for their growth, and (d) part of the cell suspension is sampled at selected time intervals, it being understood that (e) the culturing of the bacteria is continued in the culture chamber after each step of partial sampling of the bacterial suspension.

In certain embodiments of a continuous culture method, steps (d) and (e) can be repeated a number of times ranging from 2 to 1000 times, for example from 1 to 100 times, or in certain cases from 1 to 10 times.

In certain embodiments, the magnetosome chains are extracted from the cells which are harvested at the end of the actual culturing process. By way of illustration, the magnetosome chains can be extracted according to a method comprising the following steps:

(i) lysis of the cells harvested at the end of culturing thereof, for example by sonication, in order to obtain a liquid containing magnetosome chains and cell debris in suspension, (ii) separation of the magnetosome chains and of the cell debris by applying a magnetic field to the solution obtained at the end of step (i), for example using a powerful magnet (for example a magnet having a power ranging from 0.1 to 1 T), (iii) recovery of the separated magnetosome chains, for example by removal of the supernatant containing the cell debris and recovery of a magnetosome pellet.

Generally, the magnetosome chains are recovered in the form of a pellet and are then resuspended in a buffer appropriate for their future use, as is illustrated in the examples. Preferentially, a non-saline buffer medium is used.

In certain embodiments, the magnetosome chains can be selected according to their size, for example by subjecting them to magnetic fields of increasing power (for example, magnetic fields having a power ranging from 0.05 to 1 T), or else by subjecting them to a size exclusion chromatography step.

The magnetosome chains obtained from the magnetotactic bacteria cultured in the presence of at least one chelating agent are of use in particular for treating cancers by thermotherapy. Thus, the magnetosome chains obtained by culturing the magnetotactic bacteria in the presence of at least one chelating agent can be used in vivo for destroying tumor cells, owing to a local generation of heat when said magnetosome chains are subjected to an alternating magnetic field.

EXAMPLES

Example 1

Culturing of Magnetotactic Bacteria and Extraction of Magnetosomes 1.1. Bacteria Magnetotactic bacteria of the *Magnetospirillum magneticum* species, strain AMB-1, available from ATCC under the reference ATCC No. 700274, were used.

The cells were placed in culture under microanaerobic conditions, i.e. in a culture medium which has not been degassed but which is closed and has no contact with oxygen. The bacteria were cultured at laboratory temperature (approximately 25° C.) in a liquid culture in a slightly modified MSGM medium (medium ATCC 1653), the makeup of which is described hereinafter.

1.2. Control Culture Medium

For a volume of one liter, the culture medium contains 0.68 g of monobasic potassium phosphate, 0.85 g of sodium succinate, 0.57 g of sodium tartrate, 0.083 g of sodium acetate, 225 µl of resazurin at 0.2%, 0.17 g of sodium nitrate, 0.04 g of L-ascorbic acid, 2 ml of a 10 mM iron quinate solution, 10 ml of a Woolf vitamin solution and 5 ml of a Woolf mineral solution.

The iron quinate solution was prepared by dissolving 0.19 g of quinic acid and 0.29 g of $FeCl_3.6H_2O$ in 100 milliliters of distilled water.

The Woolf mineral solution contains, in 1 liter of distilled water, 0.5 g of nitrilotriacetic acid (NTA, $C_6H_9NO_6$), 1.5 g of magnesium sulfate hepta ($MgSO_4.7H_2O$), 1 g of sodium chloride, 0.5 g of manganese sulfate ($MnSO_4.H_2O$), 100 mg of iron sulfate heptahydrate ($FeSO_4.7H_2O$), 100 mg of cobalt nitrate ($CO(NO_3)_2.7H_2O$), 100 mg of calcium chloride ($CaCl_2$), 100 mg of zinc sulfate heptahydrate ($ZnSO_4.7H_2O$), 10 mg of copper sulfate pentahydrate ($CuSO_4.5H_2O$), 10 mg of potassium aluminum sulfate dodecahydrate ($AlK(SO_4).12H_2O$), 10 mg of boric acid ($H_3BO_3$), 10 mg of sodium molybdate ($Na_2MoO_4.2H_2O$), 2 mg of sodium selenite ($Na_2SeO_3$), 10 mg of sodium tungstate dihydrate ($Na_2WO_4.2H_2O$) and 20 mg of nickel chloride ($NiCl_2.6H_2O$).

The Woolf vitamin solution was prepared by dissolving, in one liter of distilled water, 2.2 mg of folic acid (vitamin B9), 10.2 mg of pyridoxine (vitamin B6), 5.2 mg of riboflavin (vitamin B2), 2.2 mg of biotin (vitamin H or B7), 5.2 mg of thiamine (vitamin B1), 5.2 mg of nicotinic acid (vitamin B3 or PP), 5.2 mg of pantothenic acid (vitamin B5), 0.4 mg of vitamin B12, 5.2 mg of aminobenzoic acid, 5.2 mg of thiotic acid and 900 mg of potassium phosphate.

The pH of the medium was adjusted to 6.85 using a 5M sodium hydroxide solution.

1.3 Culture Medium Containing the Iron-Chelating Agents:

In order to prepare the culture medium containing the various iron-chelating agents, said agents were introduced at various concentrations into the culture medium described above (section 1.2).

1.4. Magnetosome Chain Extraction

The cells were harvested during the stationary phase. The stationary phase occurs when the culture medium is completely reduced, as indicated by a color change, from pink to colorless.

The cells are harvested during the stationary phase by centrifugation at 4000 g for 20 minutes. The supernatant is removed and the cells are resuspended in 3 ml of deionized water.

To extract the magnetosome chains, 1 ml of cell suspension obtained as described above is again centrifuged and then resuspended in a 10 mM Tris-HCl buffer at pH 7.4, and then the cell suspension is subjected to a sonication step for 120 minutes at a power of 30 W, in order to lyze the cells and to release the magnetosome chains. Sonication periods of 60 and 180 minutes can also be used. For a sonication period of less than 60 minutes, the bacteria are not all lyzed. For a sonication period of greater than 180 minutes, the beginnings of aggregation are observed owing to the presence of individual magnetosomes which are aggregated.

After sonication, the magnetosome chain suspension is separated by placing a powerful neodynium magnet (0.1-1 T) in proximity to the tube, and the magnetic material is then recovered in the form of a pellet.

The supernatant containing the cell debris and other organic molecules is removed.

The magnetosome chains are washed 10 to 20 times in deionized water at pH 7.4 and are then resuspended in deionized sterile water.

1.5. Measurement of the Magnetic Properties:

The maghemite concentration of a suspension of magnetosome chains extracted from magnetotactic bacteria was measured using the measurement of the absorption at 480 nm of this suspension. The method of calibration between the value of the absorption and the amount of maghemite is described elsewhere (PCT/EP2010/067765). These measurements were carried out in order to determine the amount of magnetosome chains produced by the magnetotactic bacteria after a given growth time. The amounts of magnetosome chains produced in the absence and in the presence of the chelating agents were then compared.

The magnetic moment of various suspensions of magnetotactic bacteria deposited on blotting paper, under the application of a magnetic field of 500 Oe or of 1000 Oe, was also measured. The magnetic moment was measured for 10 ml of suspension of magnetotactic bacteria harvested at various days of growth, centrifuged, and then resuspended in 100 µl of distilled water. These 100 µl containing the magnetotactic bacteria are then redeposited on nonmagnetic absorbent paper which itself is inserted into a capsule that is placed in the magnetometer in order to carry out the magnetic measurements. Since the value of the magnetic moment is proportional to the amount of magnetosomes present in the sample, the measurement thereof indicates the presence or absence of magnetosomes. When a zero magnetic moment is measured, this indicates that the amount of magnetosomes present in the sample is so low (or zero) that it is not detectable using the magnetometer (a very sensitive SQUID).

Example 2

Influence of the Presence of Chelating Agents in the Culture Medium on Bacterial Growth and the Number of Magnetosomes, Measured after 7 Days of Culture In this example, the magnetotactic bacteria were cultured in the presence of various chelating agents and harvested after 7 days. The absorption and the iron oxide concentration of the magnetosome chains extracted from the bacteria were then measured.

As shown in FIGS. 1(a), 1(c), 2(a) and 2(c), the absorption values measured at 565 nm of the suspensions of magnetotactic bacteria cultured in the presence of chelating agents are greater than those of the suspensions of bacteria cultured in the absence of chelating agents, for a large number of chelating agents and of concentrations tested. These are hemoglobin at the concentrations of 0.4 µM, 4 µM and 40 µM (FIG. 1(a)), EDTA at the concentrations of 0.4 µM, 4 M and 40 µM (FIG. 1(a)), anthranilic acid at the concentration of 0.4 µM (FIG. 1(a)), citric acid at the concentrations of 4 µM and 40 µM (FIG. 1(c)), 3-(N-morpholino)propanesulfonic acid at the concentrations of 4 µM and 40 µM (FIG. 1(c)), 3-[cyclohexylamino]-1-propanesulfonic acid at the concentrations of 0.4 µM, 4 µM and 40 µM (FIG. 1(c)), neridronate at the concentration of 40 µM (FIG. 2(a)), nicotinamide at the concentration of 40 µM (FIG. 2(a)), rhodamine B at the concentrations of 0.4 µM, 4 µM and 40 µM (FIG. 2(c)), calcein at the concentrations of 4 µM and 40 µM (FIG. 2(c)) and dextran at the concentration of 40 µM (FIG. 2(c)). The most pronounced effects are observed for hemoglobin at the concentration of 40 µM, citric acid at the concentration of 4 µM, nicotinamide at the concentration of 40 µM and calcein at the concentration of 40 µM, for which the absorption is 1.5 to 2 times greater than that of the control bacteria.

FIGS. 1(b), 1(d), 2(b) and 2(d) show the iron oxide concentration, proportional to the concentration of magnetosomes, of various suspensions of magnetosome chains extracted from the bacteria, for magnetotactic bacteria harvested after 7 days of culture and cultured in the presence (or absence) of a variety of chelating agents. The magnetosome production is increased compared with the control bacteria for a variety of different chelating agents introduced into the culture medium at various concentrations. This increase in magnetosome production takes place when hemoglobin at the concentrations of 0.4 µM, 4 µM and 40 µM (FIG. 1(b)), EDTA at the concentrations of 0.4 µM and 4 µM (FIG. 1(b)), anthranilic acid at the concentration of 0.4 µM (FIG. 1(b)), citric acid at the concentrations of 4 µM and 40 µM (FIG. 1(d)), 3-(N-morpholino)propanesulfonic acid at 0.4 µM (FIG. 1(d)), 3-(cyclohexylamino)-1-propanesulfonic acid at the concentrations of 0.4 µM, 4 µM and 40 µM (FIG. 1(d)), alendronate at the concentrations of 0.4 µM, 4 µM and 40 µM (FIG. 2(b)), dextran at the concentration of 40 µM (FIG. 2(d)), calcein at the concentrations of 4 µM and 40 µM (FIG. 2(d)) and rhodamine B at the concentrations of 0.4 µM, 4 µM and 40 µM are introduced into the culture medium of the magnetotactic bacteria. The most pronounced effects are observed with hemoglobin, for which the iron oxide production is increased by a factor of 7-8 for a hemoglobin concentration in the culture medium of 0.4 µM or 4 µM (FIG. 1(b)).

The following conclusions can be drawn from this example:
(i) The number of bacteria and the magnetosome production are both higher in the presence of chelating agents than in the absence of chelating agents, for a large number of chelating agents and of concentrations tested.
(ii) The 400 µM concentration is the maximum concentration of chelating agents above which neither bacterial growth nor magnetosome production are stimulated (FIGS. 1 and 2).
(iii) The magnetosome production generally increases more than the number of bacteria in the presence of chelating agents (cf. the example of hemoglobin). This suggests that, in the presence of chelating agents, the stimulation of bacterial growth is accompanied either by an increased number of magnetosomes per magnetotactic bacterium, or by a lower percentage of bacteria not producing magnetosomes.

Example 3

Effects of Chelating Agents on Bacterial Growth

A. Materials and Methods

Cultures of *Magnetospirillum magneticum* were prepared as described in example 1. The bacteria were cultured in 10 milliliter tubes. A volume of 100 microliters of culture medium was inoculated, at time "D0" (Day 0), with $0.1 \times 10^6$ bacterial cells. The cultures in suspension were placed at ambient temperature (approximately 25° C.) and the growth of the bacteria over time was monitored by measuring O.D. at the wavelength of 565 nanometers.

The following series of culture samples were prepared:
  samples of control culture, comprising the bacterial cells in the culture medium free of chelating agent;
  a series of culture samples containing the chelating agent rhodamine B, at increasing concentrations of 0.4 µM, 4 µM, 40 µm and 400 µM;
  a series of culture samples containing the chelating agent ascorbic acid, at increasing concentrations of 0.4 µM, 4 µM, 40 µM and 400 µM;
  a series of culture samples containing the chelating agent erythrosine, at increasing concentrations of 0.4 µM, 40 µM and 400 µM;
  a series of culture samples containing the chelating agent folic acid, at increasing concentrations of 0.4 µM, 4 µM, 40 µM and 400 µM;

Several series of tests were carried out, the results of which are reported in FIGS. 3 to 10. The bacteria were cultured for 12 days in a tube and the absorbance over the whole of the spectrum ranging from 400 to 700 nanometers was measured, respectively, (i) on the second day (D2) after inoculation, (ii) on the third day (D3) after inoculation, (iii) on the fourth day (D4) after inoculation, (iv) on the seventh day (D7) after inoculation, (v) on the eighth day (D8) after inoculation and (vi) on the ninth day (D9) after inoculation. The magnetic moments of various suspensions of magnetotactic bacteria deposited on blotting paper were measured on days D7, D8 and D9.

B. Results

Figure 3A:
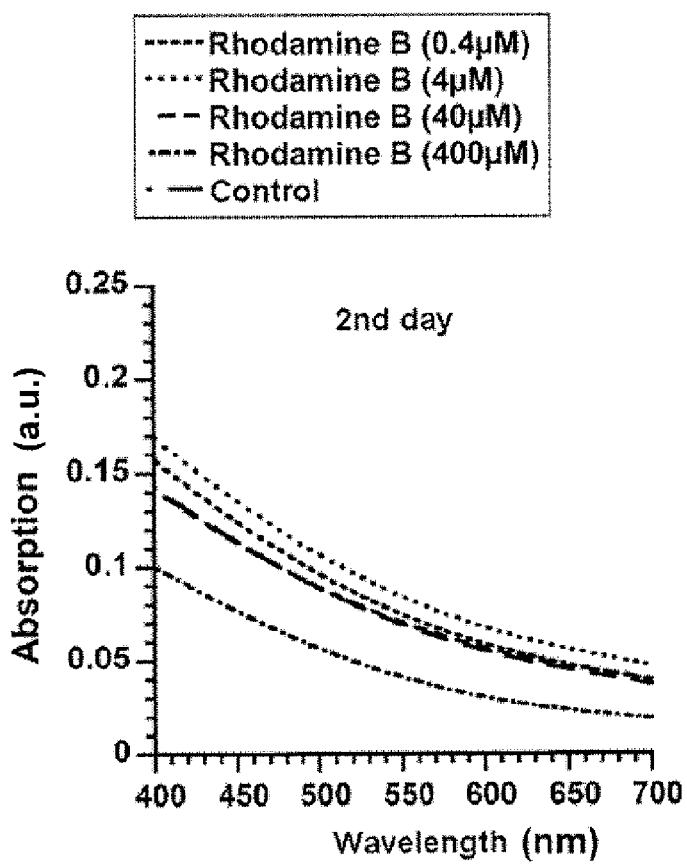
FIG. 3 shows the absorption spectra of the magnetotactic bacteria cultured in the presence of various concentrations of rhodamine B (0.4 µM, 4 µM, 40 µM and 400 µM) on the second day (3A), third day (3B), fourth day (3C), seventh day (3D), eighth day (3E) and ninth day (3F), after the inoculation of 100 µl of bacteria in tubes containing 10 ml of culture medium. Along the y-axis: absorbance values, expressed in arbitrary units (a.u.). Along the x-axis: wavelength, expressed in nanometers.
Figure 3B:
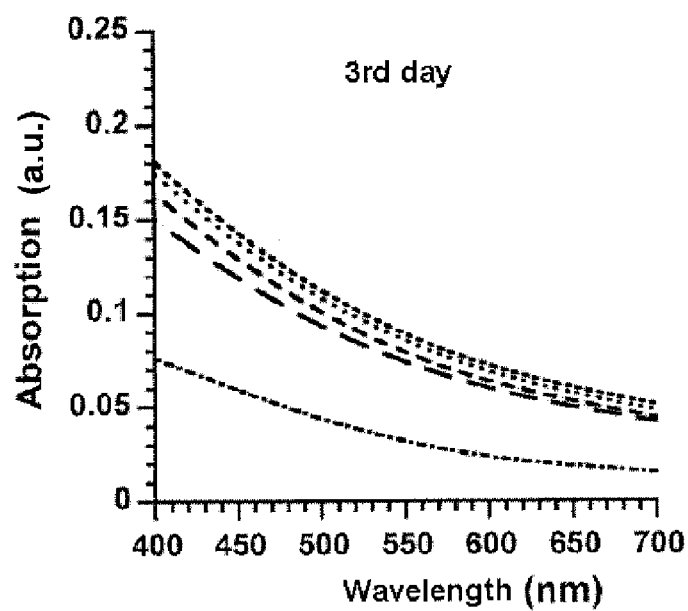
Figure 3C:
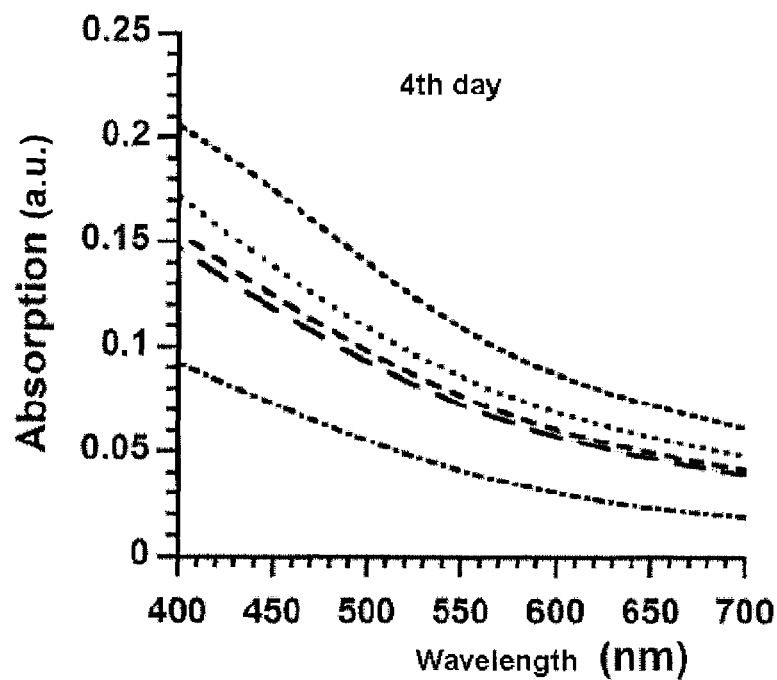
Figure 3D:
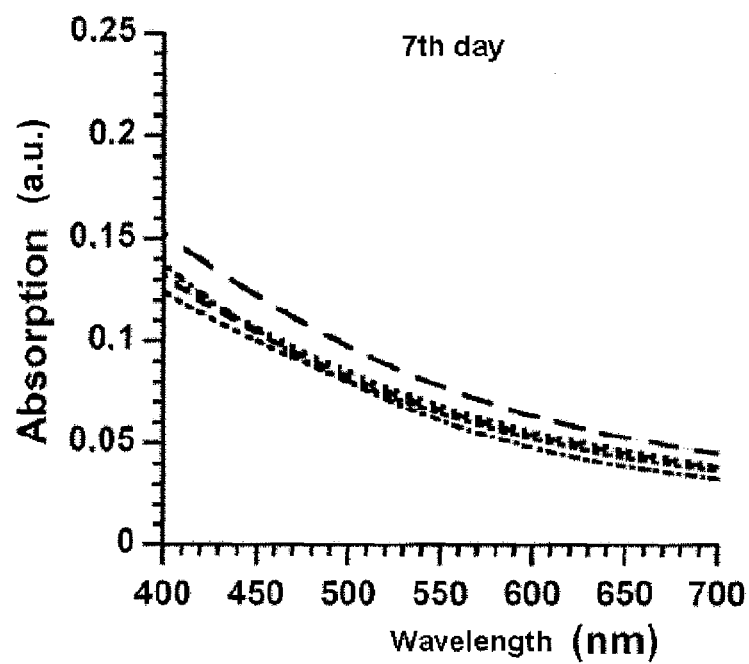
Figure 3E:
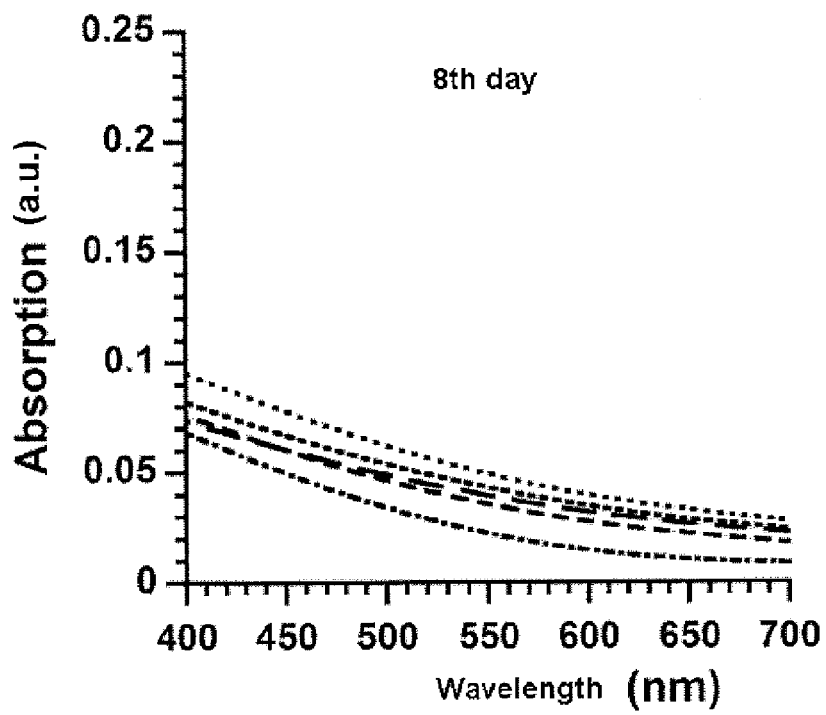
Figure 3F:
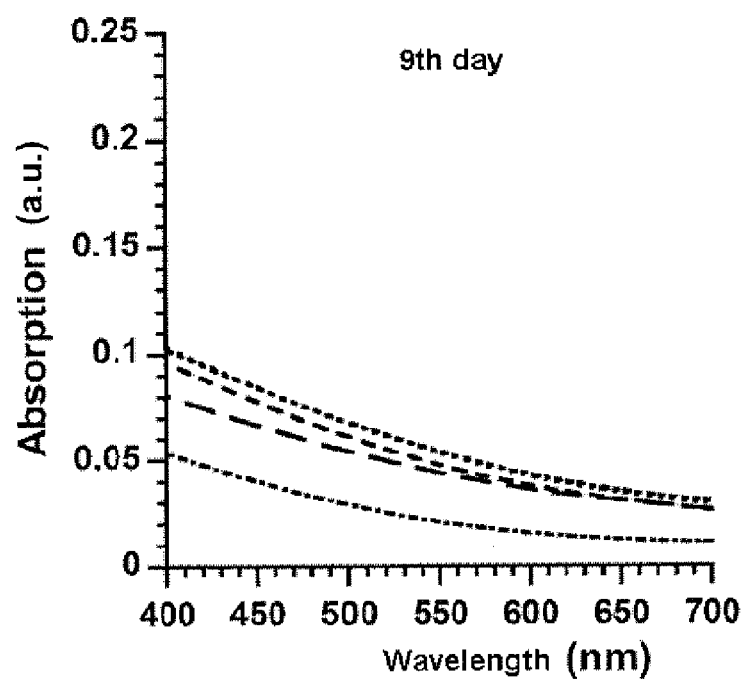
Figure 4A:
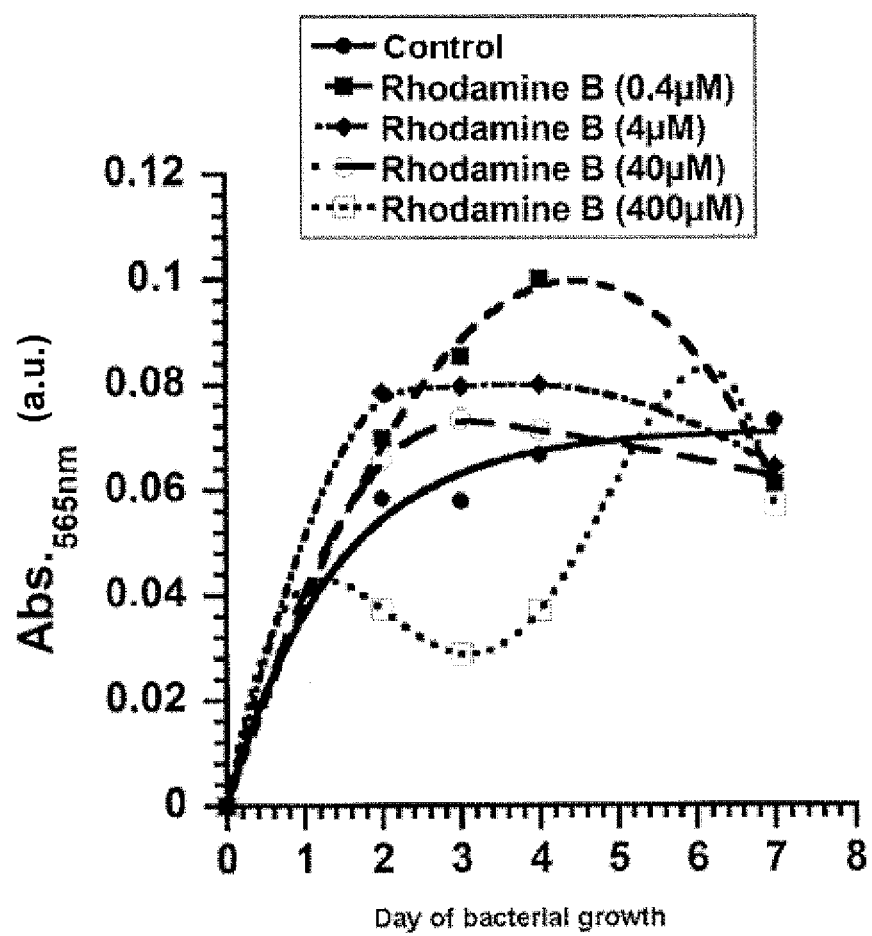
FIG. 4A shows the variation in the absorption as a function of the day of growth of the bacteria in a medium containing various concentrations of rhodamine B. Along the y-axis: absorbance values at 565 nanometers, expressed in arbitrary units (a.u.). Along the x-axis: bacterial culture time, expressed in days.
Figure 4B:
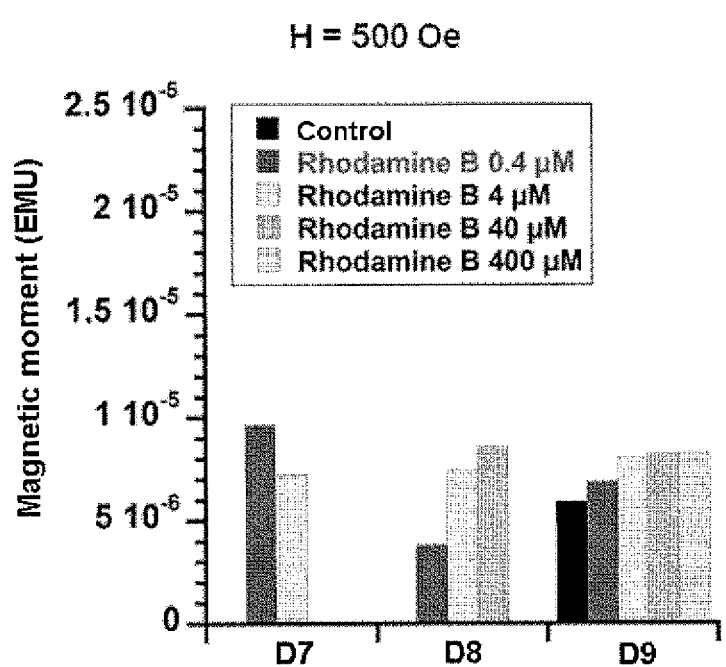
FIG. 4B shows the variation in the magnetic moment measured at 500 Oe using an MPMS-5S SQUID, on the seventh day (D7), eighth day (D8) and ninth day (D9) following the inoculation of 100 µl of bacteria in 10 ml tubes containing culture medium with increasing concentrations of rhodamine B of 0.4 µM, 4 µM, 40 µM and 400 µM. Along the y-axis: value of the magnetic moment, expressed in EMU units. Along the x-axis: culture time, expressed in days.
Figure 4C:
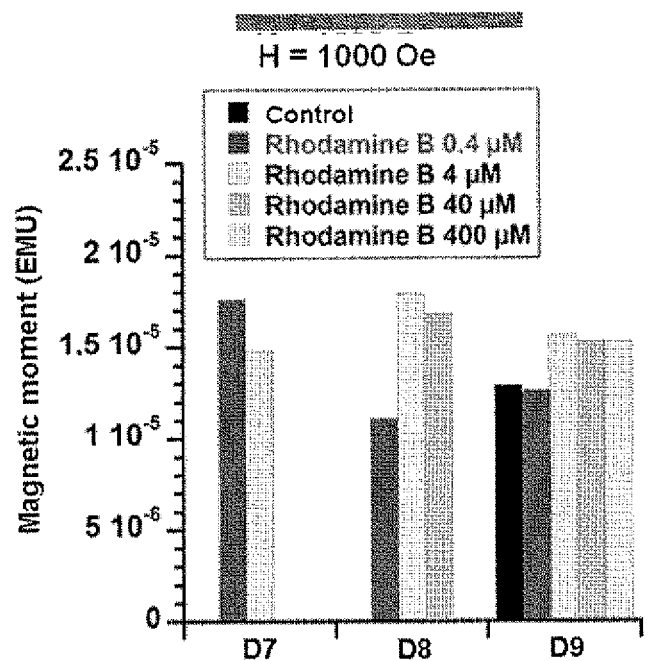
FIG. 4C shows the variation in the magnetic moment measured at 1000 Oe using an MPMS-5S SQUID, on the seventh day (D7), eighth day (D8) and ninth day (D9) following the inoculation of 100 µl of bacteria in 10 ml tubes containing culture medium with increasing concentrations of rhodamine of 0.4 µM, 4 µM, 40 µM and 400 µM. Along the y-axis: value of the magnetic moment, expressed in EMU units. Along the x-axis: culture time, expressed in days.
Figure 5A:
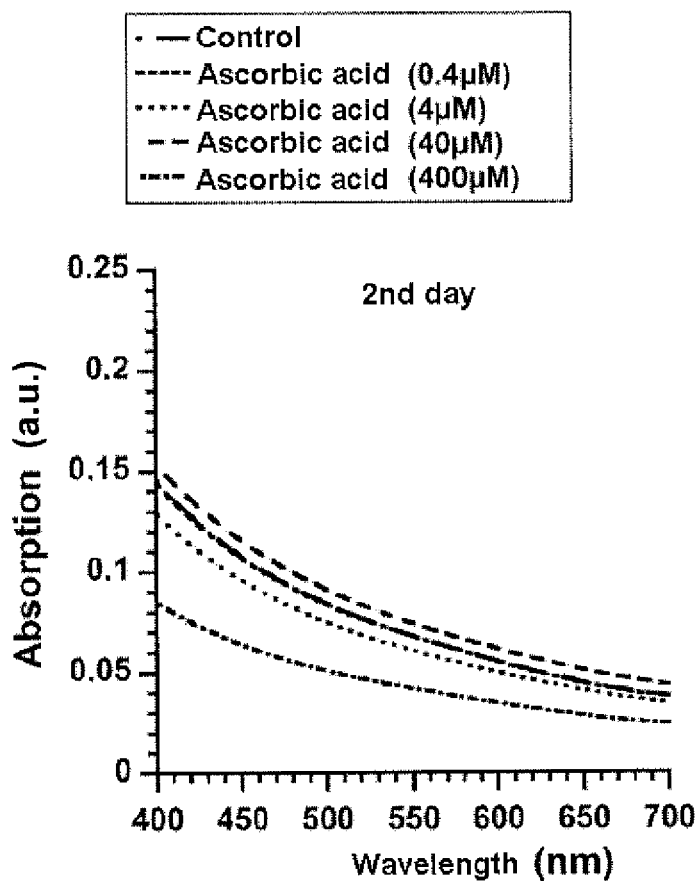
FIG. 5 shows the absorption spectra of magnetotactic bacteria cultured in the presence of various concentrations of ascorbic acid (0.4 µM, 4 µM, 40 µM and 400 µM) on the second day (5A), third day (5B), fourth day (5C), seventh day (5D), eighth day (5E), and ninth day (5F), after the inoculation of 100 µl of bacteria in tubes containing 10 ml of culture medium. Along the y-axis: absorbance values, expressed in arbitrary units (a.u.). Along the x-axis: wavelength, expressed in nanometers.
Figure 5B:
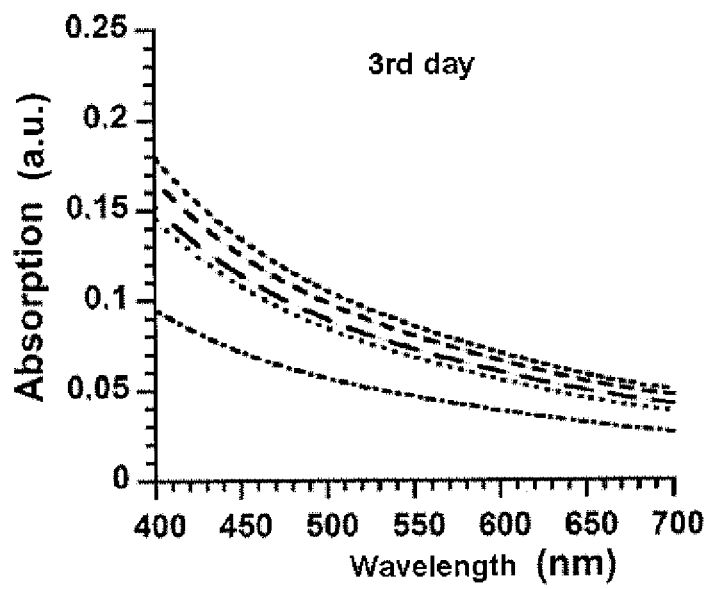
Figure 5C:
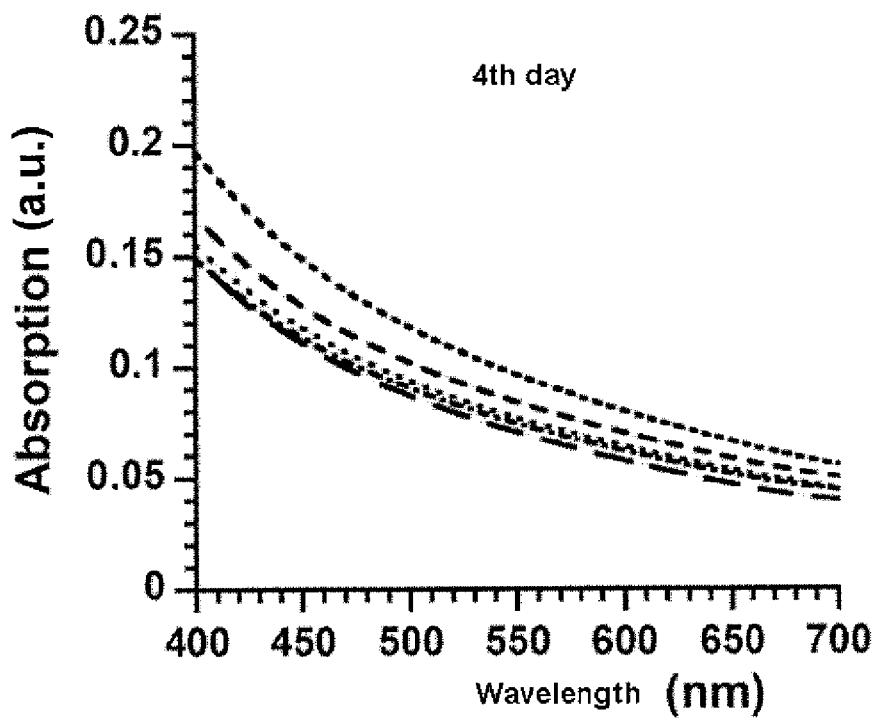
Figure 5D:
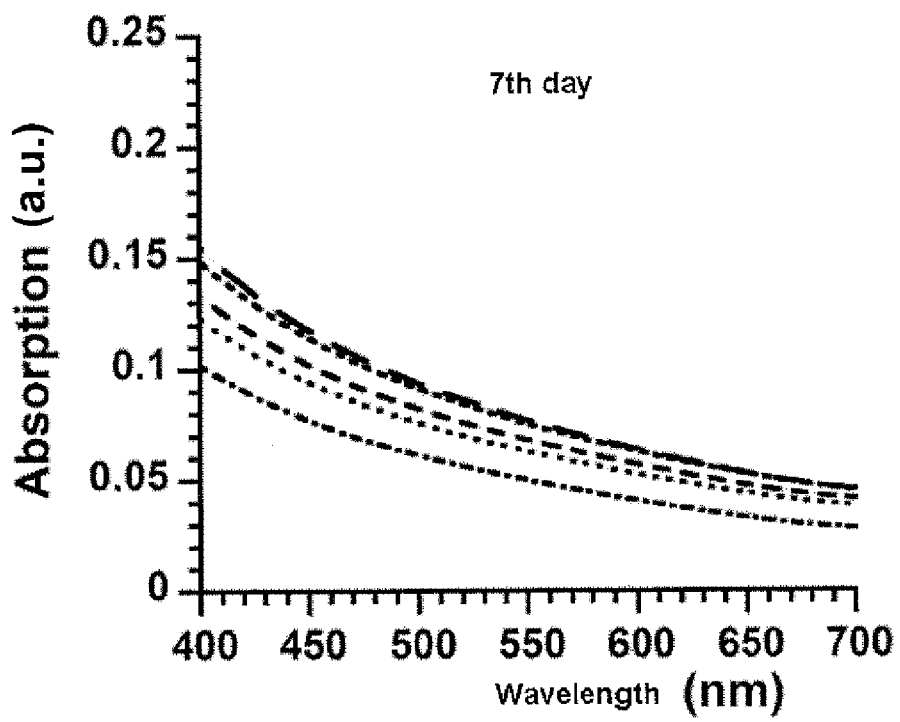
Figure 5E:
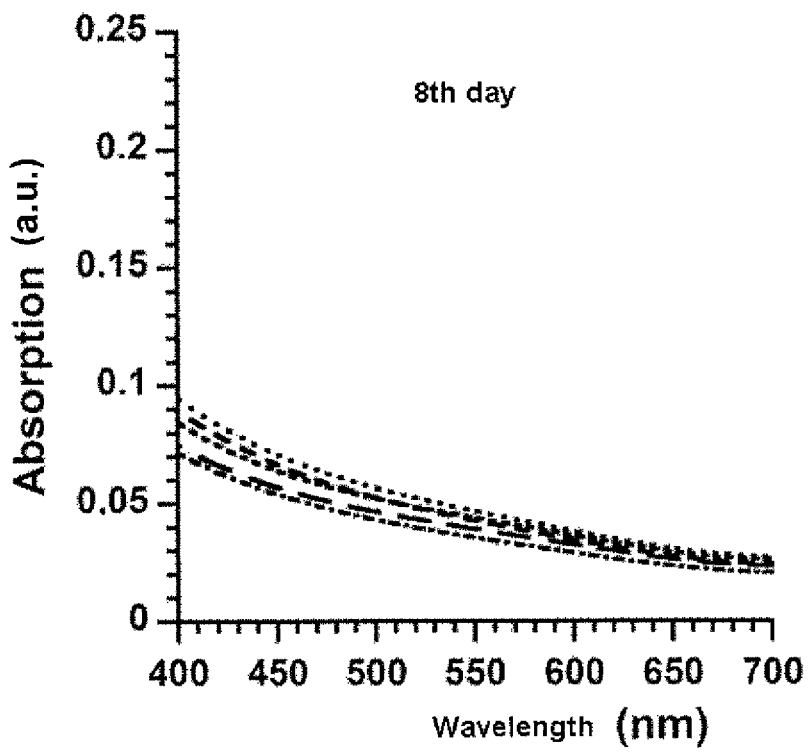
Figure 5F:
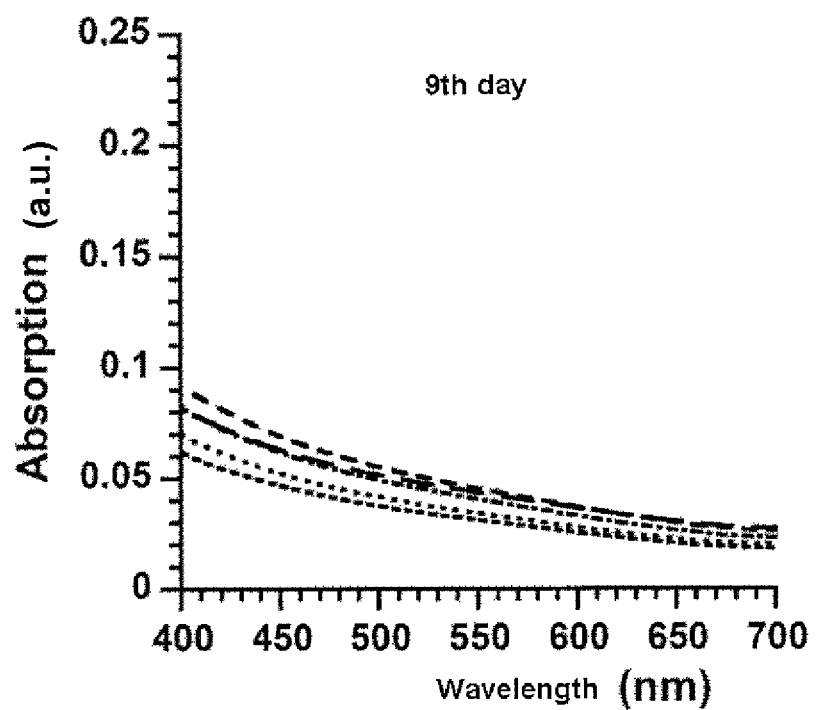

The results of FIGS. 3(a) to 3(f) show that rhodamine B stimulates the growth of the magnetotactic bacteria, as is observed by the increase in absorbance of the cell suspensions cultured in the presence of this chelating agent, compared with the cell suspensions cultured in the absence of rhodamine B. The stimulation of the bacterial growth by rhodamine B is dependent on the final concentration of chelating agent, a maximum growth stimulation being observed in this test for a final concentration of 0.4 µM to 40 µM. The 400 µM concentration is rather unfavorable to cell growth, this effect possibly being due to a certain cytotoxicity of rhodamine B, at a high concentration. The effects of rhodamine B are the greatest for the first six days of culture, i.e. during the exponential growth phase. FIG. 3(c) shows that the greatest effect is observed on the fourth day of culture (D4). The variations, during the first 7 days of growth, in the absorption as a function of the day of growth of the suspensions containing magnetotactic bacteria cultured in the presence of rhodamine were fitted (curves adjusted) with polynomes (FIG. 4(a)). The growth curves for the bacteria cultured in the presence of rhodamine B are above those of the bacteria cultured in the absence of rhodamine B (except for the rhodamine B concentration 400 µM, FIG. 4(a)). This confirms the stimulating effect of rhodamine B on bacterial growth. The magnetic moments of the bacteria were also measured on days D7, D8 and D9 under the application of a magnetic field of 500 Oe (FIG. 4(b)) or 1000 Oe (FIG. 4(c)). FIGS. 4(b) and 4(c) show the earlier appearance, i.e. on D7, of the magnetic moment for the bacteria cultured in the presence of 0.4 µM or 4 µM rhodamine B than for those cultured in the absence of rhodamine B, where the magnetic moment is measurable only on D9. These results indicate that, in the presence of 0.4 µM or 4 µM of rhodamine B, the magnetosomes are synthesized more rapidly by the magnetotactic bacteria than in the absence of rhodamine B.

Figure 6A:
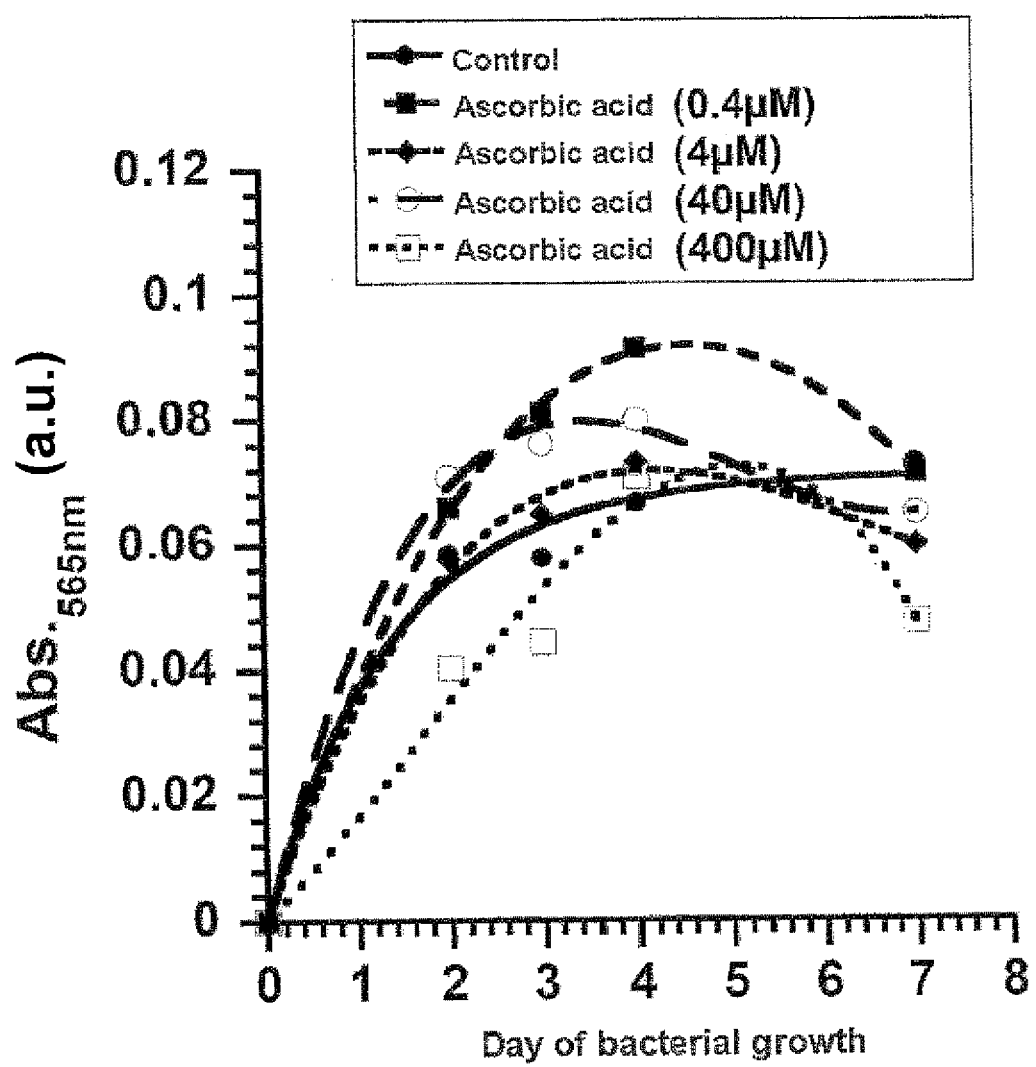
FIG. 6A shows the variation in the absorption as a function of the day of bacterial growth in a medium containing increasing concentrations of ascorbic acid of 0.4 µM, 4 µM, 40 µM and 400 μM. Along the y-axis: absorbance values at 565 nanometers, expressed in arbitrary units (a.u.). Along the x-axis: bacterial culture time, expressed in days.
Figure 6B:
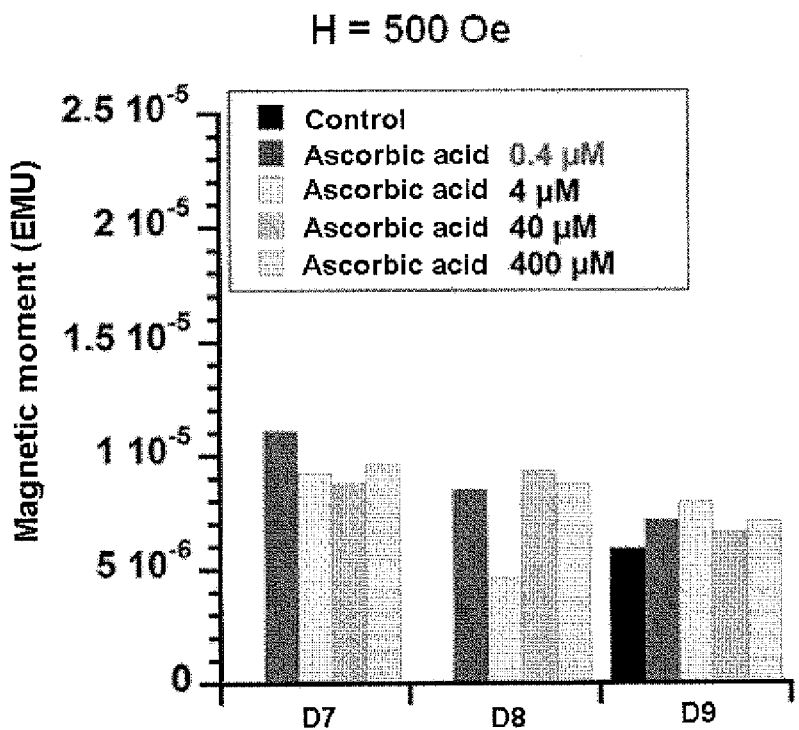
FIG. 6B shows the variation in the magnetic moment measured at 500 Oe using an MPMS-5S SQUID, on the seventh day (D7), eighth day (D8) and ninth day (D9) following the inoculation of 100 μl of bacteria in 10 ml tubes containing culture medium with increasing concentrations of ascorbic acid of 0.4 μM, 4 μM, 40 μM and 400 μM. Along the y-axis: value of the magnetic moment, expressed in EMU units. Along the x-axis: culture time, expressed in days.
Figure 6C:
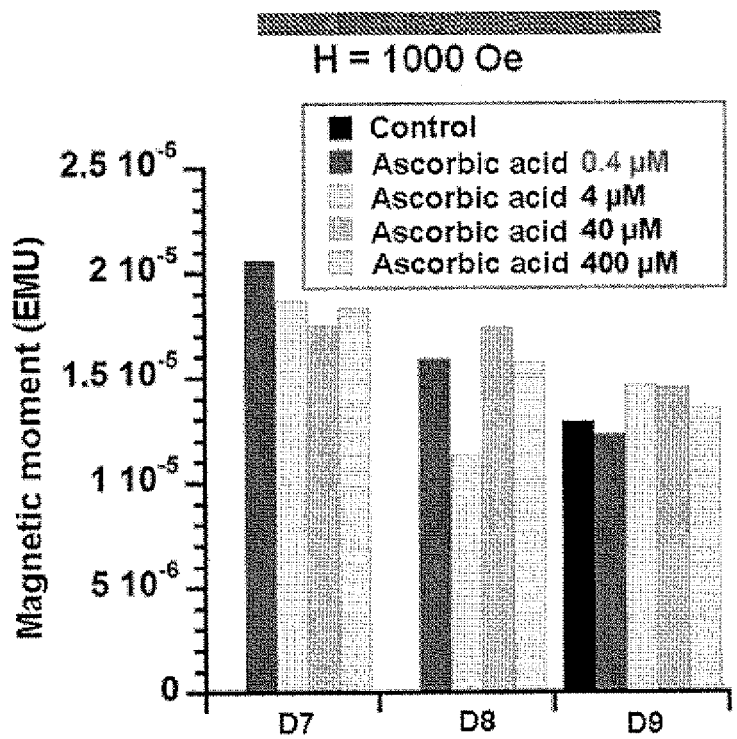
FIG. 6C shows the variation in the magnetic moment measured at 1000 Oe using an MPMS-5S SQUID, on the seventh day (D7), eighth day (D8) and ninth day (D9) following the inoculation of 100 μl of bacteria in 10 ml tubes containing culture medium with increasing concentrations of ascorbic acid of 0.4 μM, 4 μM, 40 μM and 400 μM. Along the y-axis: value of the magnetic moment, expressed in EMU units. Along the x-axis: culture time, expressed in days.
Figure 7A:
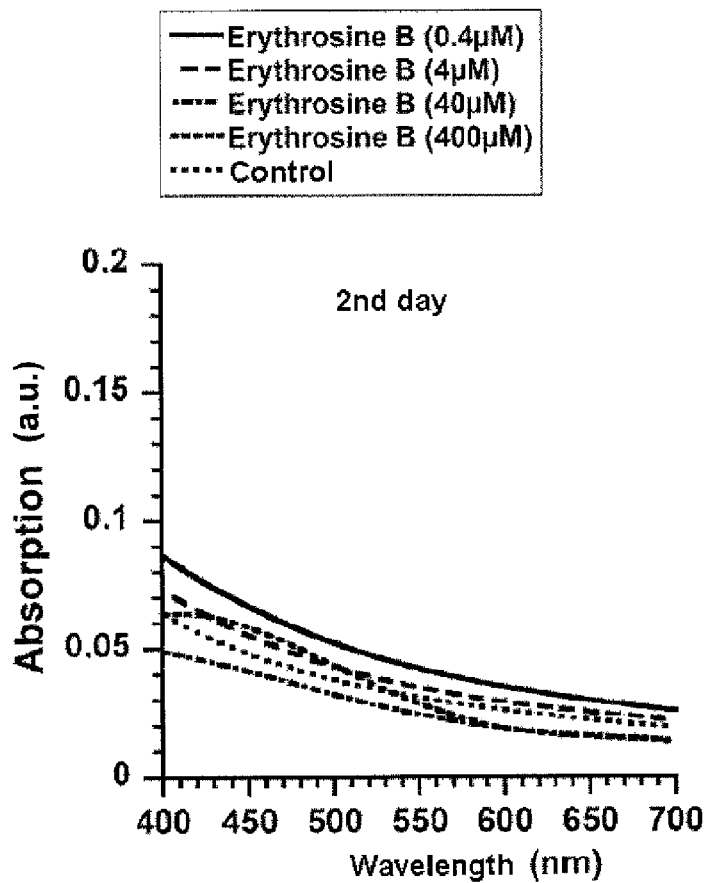
FIG. 7 shows the absorption spectra of magnetotactic bacteria cultured in the presence of various concentrations of erythrosine (0.4 μM, 4 μM, 40 μM and 400 μM) on the second day (7A), third day (7B), fourth day (7C), seventh day (7D), eighth day (7E), and ninth day (7F), after the inoculation of 100 μl of bacteria in tubes containing 10 ml of culture medium. Along the y-axis: absorbance values, measured in arbitrary units (a.u.). Along the x-axis: wavelength, expressed in nanometers.
Figure 7B:
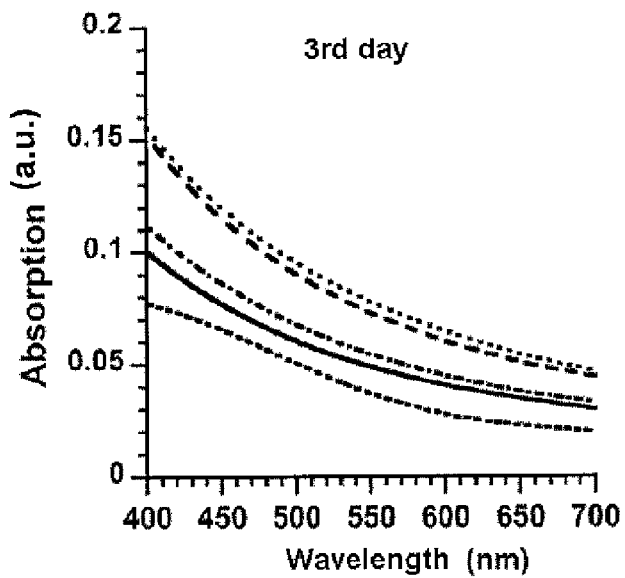
Figure 7C:
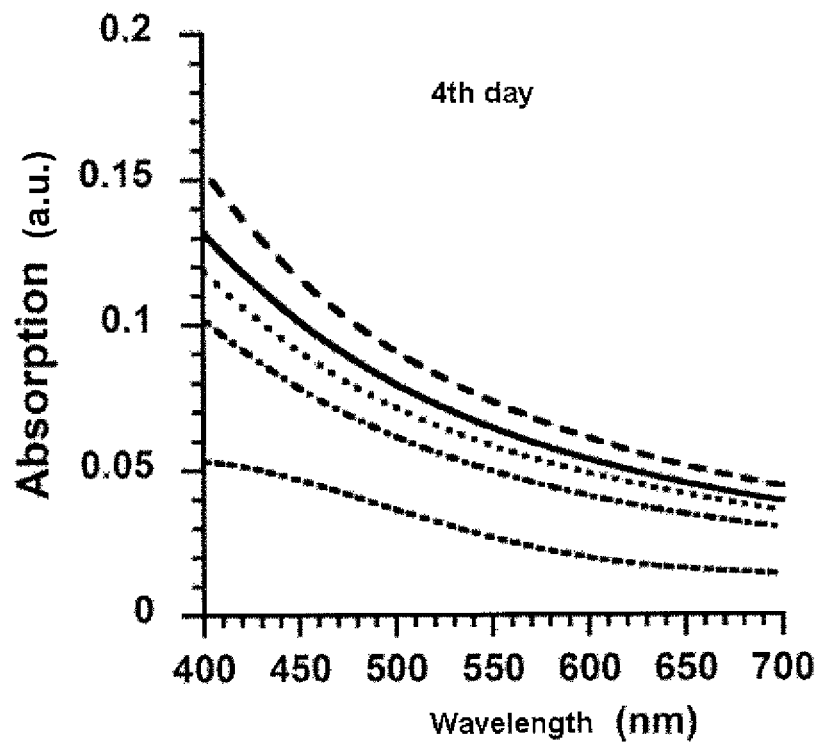
Figure 7D:
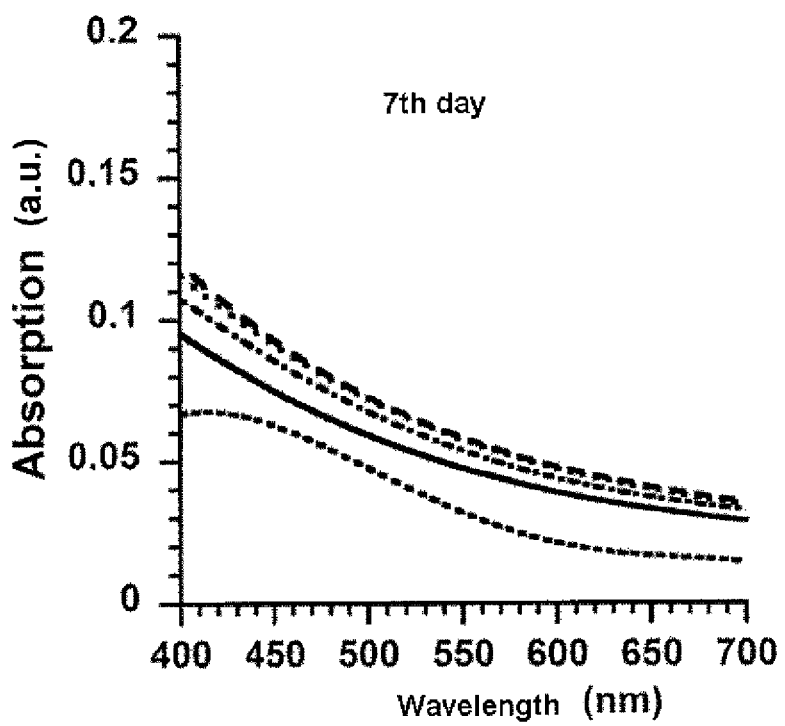
Figure 7E:
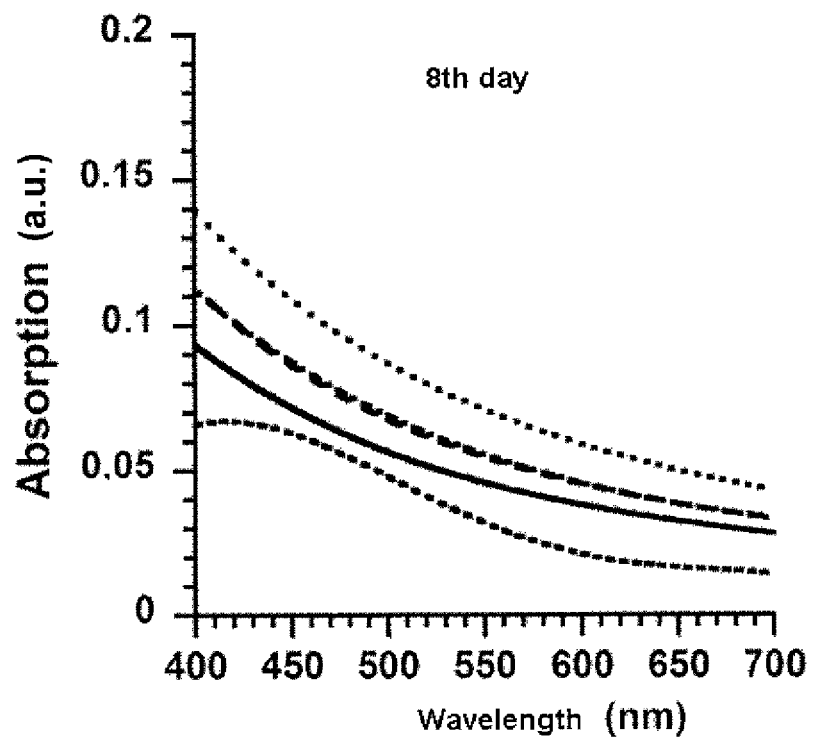
Figure 7F:
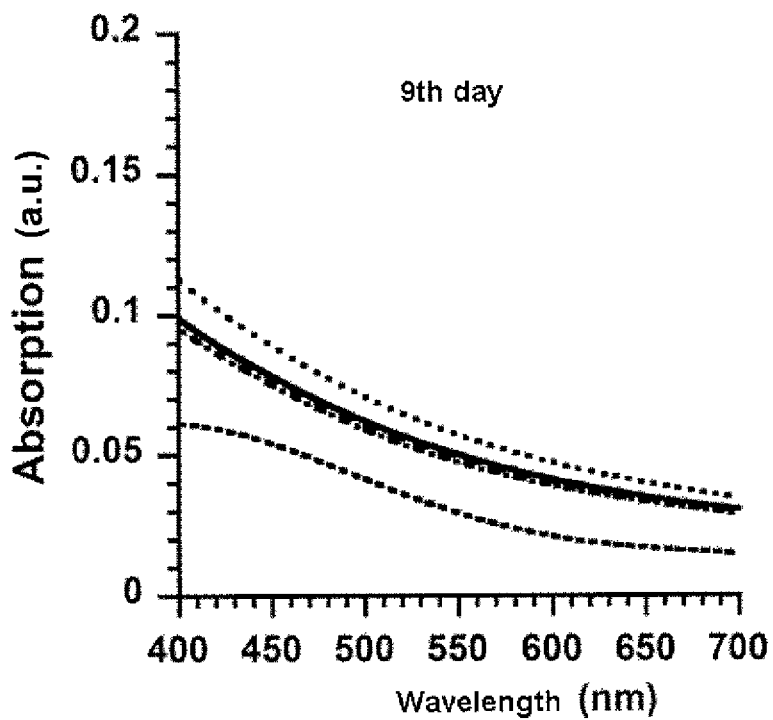

The results of FIGS. 5(a) to 5(f) show that ascorbic acid stimulates the growth of the magnetotactic bacteria, as is observed by the increase in absorbance of the cell suspensions cultured in the presence of this chelating agent, compared with the cell suspensions cultured in the absence of ascorbic acid. The stimulation of bacterial growth by ascorbic acid is dependent on the final concentration of chelating agent, maximum growth stimulation being observed in this test for a final concentration of 0.4 µM to 40 µM. The 400 µM concentration is rather unfavorable to cell growth, this effect possibly being due to a slight toxicity of ascorbic acid, at a high concentration. The effects of ascorbic acid are greater during the first four days of culture, i.e. during the exponential growth phase. The most pronounced effect is observed for 0.4 µM of ascorbic acid after 4 days of culture (FIG. 5(c)). The variations in absorption during the first 7 days of growth as a function of the day of growth of the suspensions containing magnetotactic bacteria cultured in the presence of ascorbic acid were fitted (curves adjusted) with polynomes (FIG. 6(a)). The growth curves for the bacteria cultured in the presence of ascorbic acid are, overall, above those of the bacteria cultured in the absence of ascorbic acid (except for the ascorbic acid concentration of 400 µM) (FIG. 6(a)). This confirms the stimulating effect of ascorbic acid on the bacterial growth. The magnetic moments of the bacteria were also measured on days D7, D8 and D9 under the application of a magnetic field of 500 Oe (FIG. 6(b)) or 1000 Oe (FIG. 6(c)). FIGS. 6(b) and 6(c) show the earlier appearance, i.e. on D7, of the magnetic moment for the bacteria cultured in the presence of 0.4 µM, 4 µM, 40 µM or 400 µM of ascorbic acid than in the absence of ascorbic acid, where the magnetic moment is measurable only on D9 (FIGS. 6(b) and 6(c)). These results indicate that, in the presence of 0.4 µM, 4 ∞M, 40 µM or 400 µM of ascorbic acid, the magnetosomes are synthesized more rapidly by the magnetotactic bacteria than in the absence of ascorbic acid. Compared with rhodamine B, the effect of ascorbic acid on the bacterial growth is similar, but the magnetosome production is stimulated for a wider concentration range.

Figure 8:
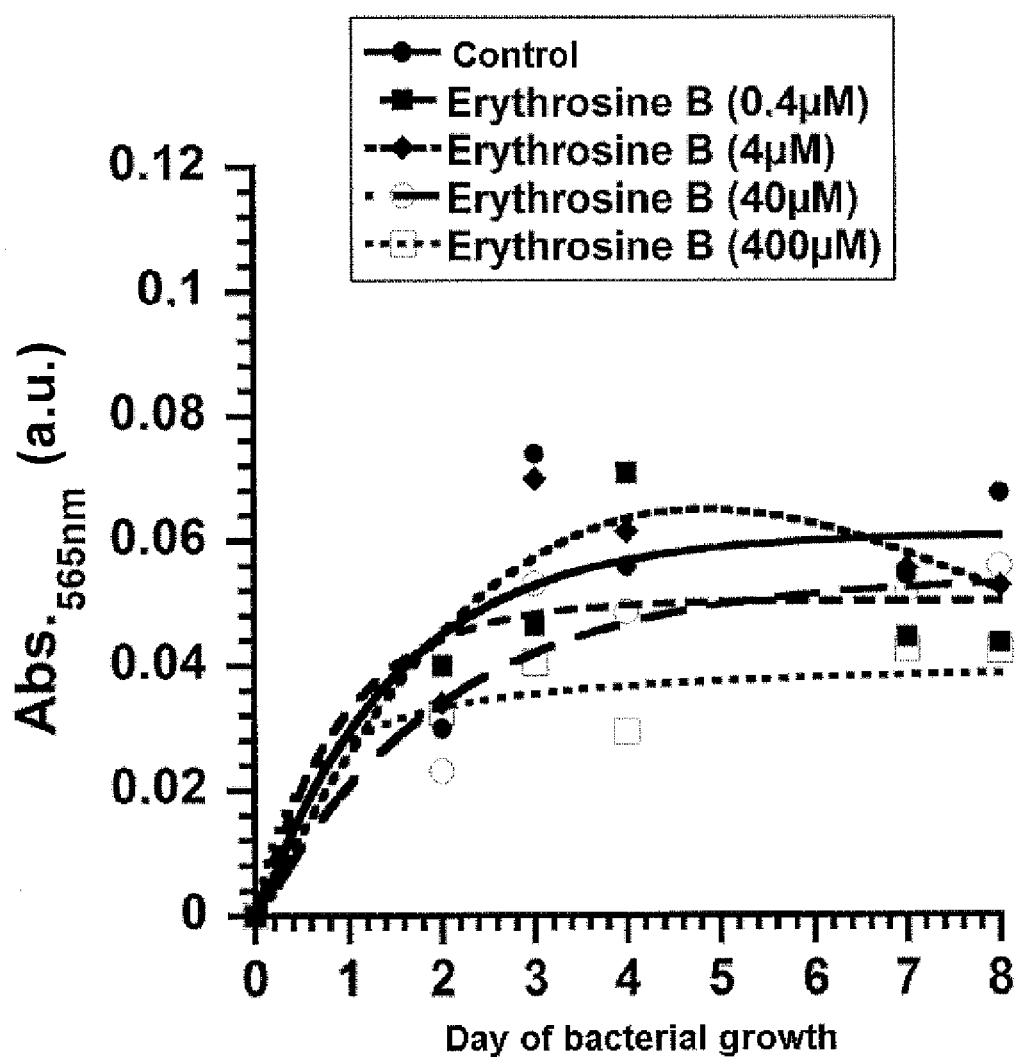
FIG. 8 shows the variation in the absorption as a function of the day of growth of the magnetotactic bacteria in a medium containing increasing concentrations of erythrosine of 0.4 μM, 4 μM, 40 μM and 400 μM. Along the y-axis: absorbance values at 565 nanometers, expressed in arbitrary units (a.u.). Along the x-axis: bacterial culture time, expressed in days.
Figure 9A:
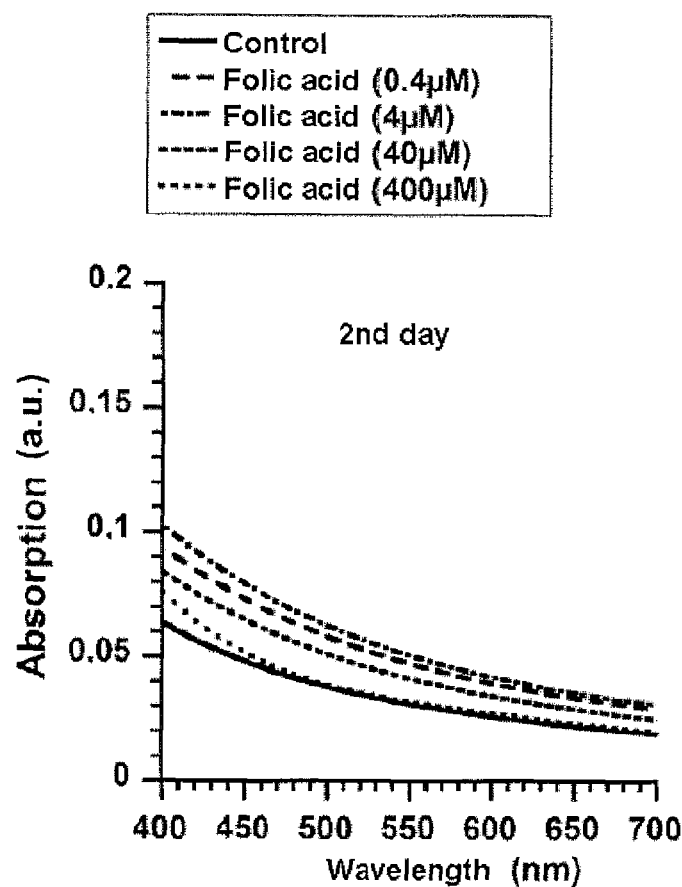
FIG. 9 shows the absorption spectra of magnetotactic bacteria cultured in the presence of various concentrations of folic acid (0.4 μM, 4 μM, 40 μM and 400 M) on the second day (9A), third day (9B), fourth day (9C), seventh day (9D), eighth day (9E), and ninth day (9F), after the inoculation of 100 μl of bacteria in tubes containing 10 ml of culture medium. Along the y-axis: absorbance values, expressed in arbitrary units (a.u.). Along the x-axis: wavelength, expressed in nanometers.
Figure 9B:
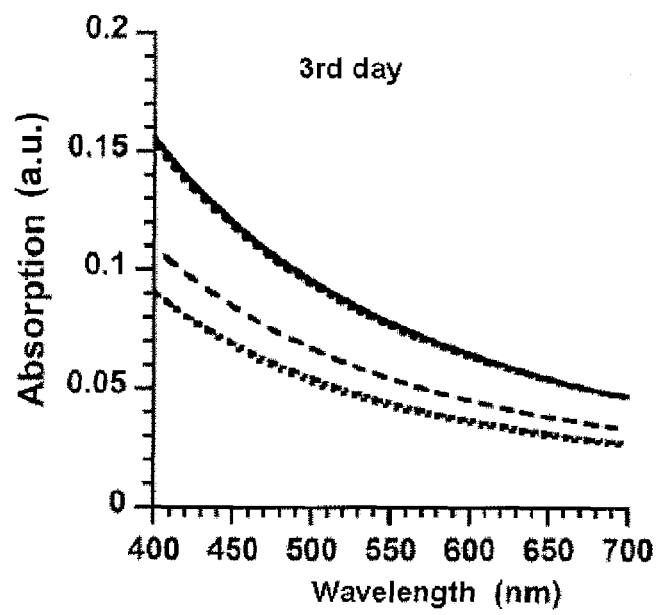
Figure 9C:
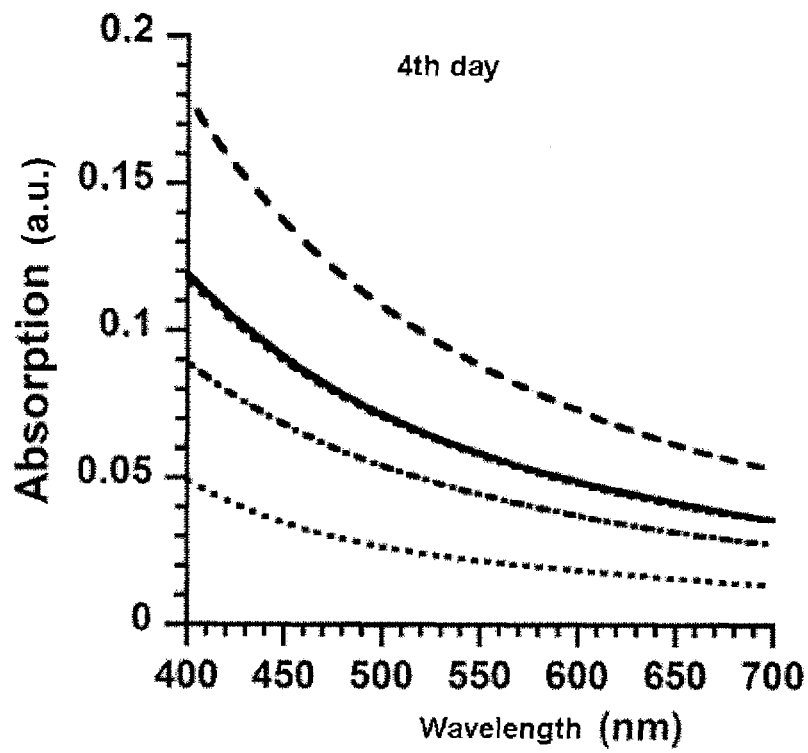
Figure 9D:
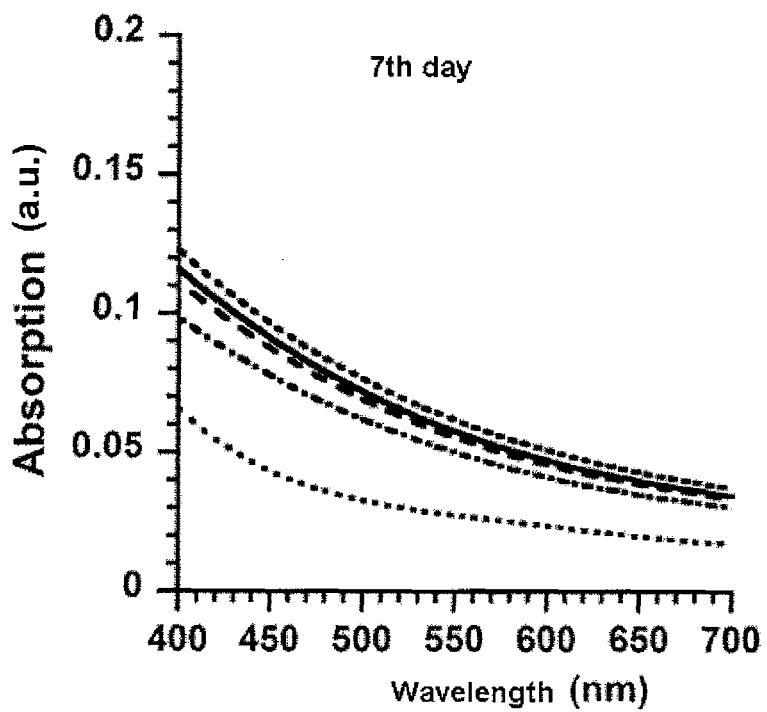
Figure 9E:
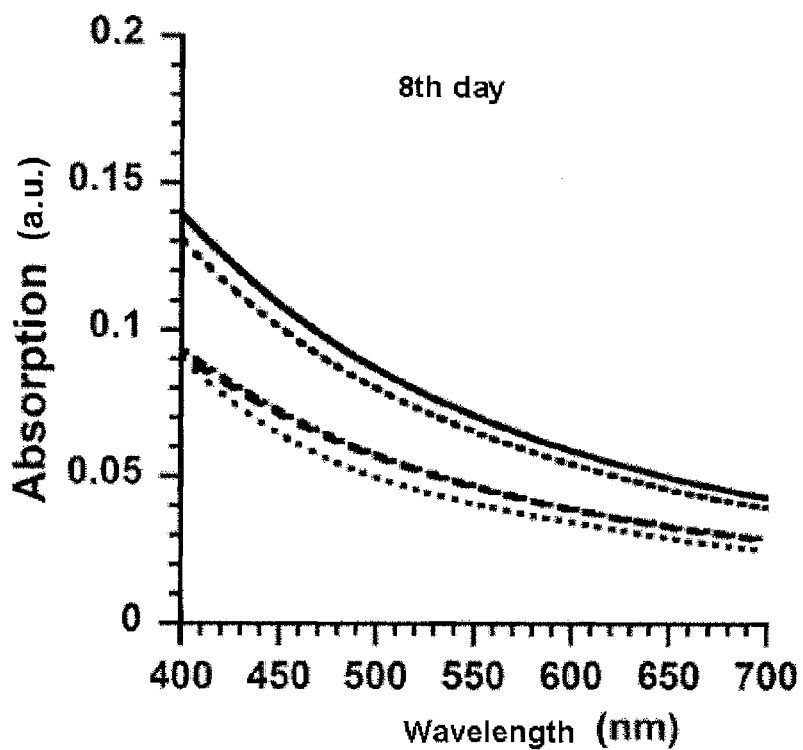
Figure 9F:
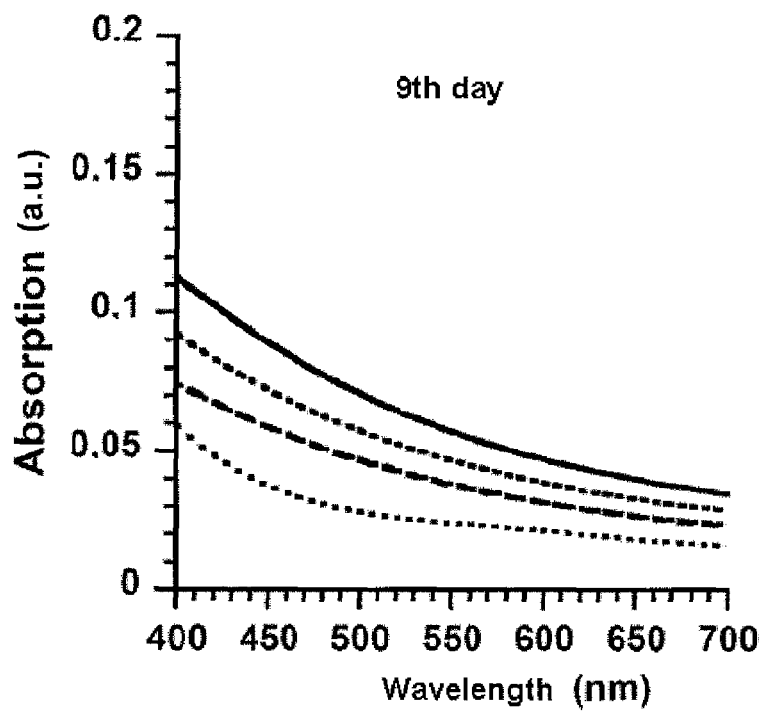

The results of FIGS. 7(a) to 7(f) and of FIG. 8 show that erythrosine stimulates the growth of the magnetotactic bacteria less than rhodamine B or ascorbic acid. A greater absorption of the magnetotactic bacteria cultured in the presence of 0.4 µM or 4 µM of erythrosine is observed on day D4. For the other days of culture and the other concentrations, the absorption of the bacteria cultured in the presence of erythrosine is either similar to or lower than the absorption of the control bacteria. This is perhaps due to the presence of iodine in erythrosine, which would be toxic for the bacteria.

Figure 10:
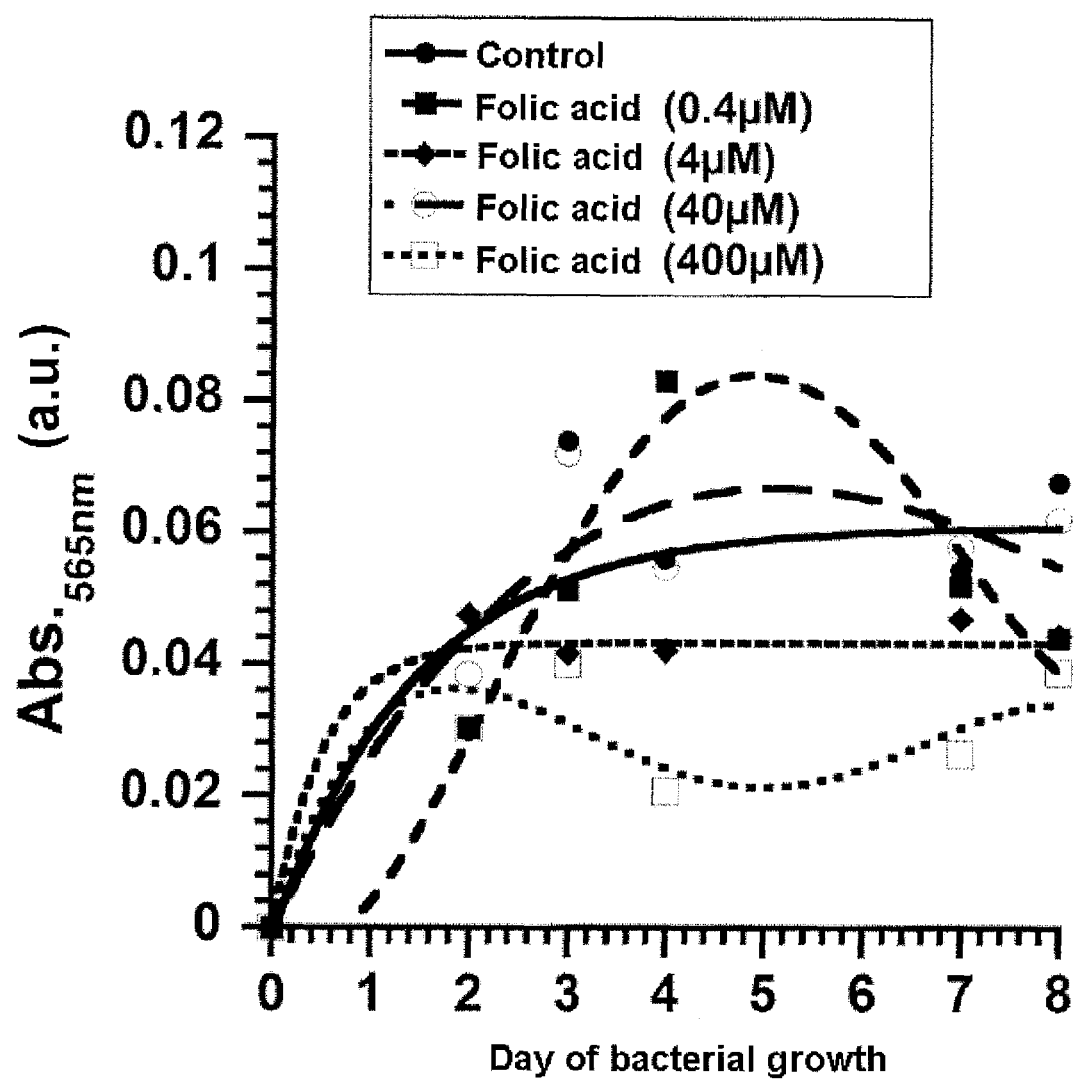
FIG. 10 shows the variation in the absorption as a function of the day of growth of the magnetotactic bacteria in a medium containing increasing concentrations of folic acid of 0.4 μM, 4 μM, 40 μM and 400 μM. Along the y-axis: absorbance values at 565 nanometers, expressed in arbitrary units (a.u.). Along the x-axis: bacterial culture time, expressed in days.

The results of FIGS. 9(a) to 9(f) and of FIG. 10 show that folic acid stimulates the growth of the magnetotactic bacteria either by allowing the bacteria to grow more rapidly during the first two days of growth (folic acid at a concentration of 4 µM, FIG. 10) or by allowing the bacteria to multiply in greater number during the first 4 days of growth (folic acid at concentrations of 0.4 µM or 40 µM).

The following conclusions can be drawn from this example:

(i) The magnetotactic bacteria grow and produce magnetosomes more rapidly for three of the chelating agents tested (rhodamine, ascorbic acid and folid acid) at concentrations ranging between 0.4 µM and 40 µM depending on the chelating agents.

(ii) The chelating agents stimulate not only bacterial growth, but also magnetosome production.

Example 4

Continuous-Flow Culture of Magnetotactic Bacteria

The stimulation of bacterial growth and of magnetosome production makes it possible to envision a continuous-flow culture system for magnetotactic bacteria. To do this, an experimental device of the Biostat®Aplus type sold by the company Sartorius may be used. According to this device, the bacterial culture medium containing the chelating agents is continuously introduced into a Biostat where the bacteria grow under controlled conditions (control of temperature, of pH, of oxygen concentration). The bacteria which are grown are then continuously recovered in a bottle. This device operates using a system of pumps which makes it possible to circulate the culture medium and the bacteria.

Since the bacteria grow more rapidly in the presence of chelating agents than in the absence of chelating agents, this device makes it possible to culture more bacteria in the presence than in the absence of chelating agents.

The invention claimed is:

1. A method comprising:
   stimulating growth of magnetotactic bacteria by culturing the bacteria in a culture medium for magnetotactic bacteria into which at least one chelating agent is added, said chelating agent being selected from the group consisting of:
   chelating agents having one or more phosphonate groups,
   chelating agents having one or more ketone groups,
   chelating agents having one or more sulfonate groups,
   rhodamine B, ascorbic acid, folic acid, a low-molecular weight dextran, anthranilic acid, porphyrin rings of hemoglobin, alendronate, calcein, erythrosine, and 3-[cyclohexylamino]1-propanesulfonic acid (CAPS),
   wherein the chelating agent is added to the culture medium at a final concentration of from 0.4 µM to 40 µM.

2. The method as claimed in claim 1, wherein said chelating agent is selected from rhodamine B, ascorbic acid, folic acid, erythrosine, porphyrin rings of hemoglobin, a low-molecular-weight dextran, anthranilic acid, calcein, alendronate, and 3-[cyclohexylamino]-1-propanesulfonic acid (CAPS).

3. A method for culturing magnetotactic bacteria comprising:
   a) adding magnetotactic bacteria to an appropriate culture medium into which a chelating agent or a combination of chelating agents is added at a final concentration ranging from 0.4 µM to 40 µM,
   b) culturing the magnetotactic bacteria in said medium, under chosen operating conditions, and
   c) recovering the magnetotactic bacterial cells obtained at the end of step b), said chelating agent being selected from the group consisting of:
   chelating agents having one or more phosphonate groups,
   chelating agents having one or more ketone groups,
   chelating agents having one or more sulfonate groups,
   rhodamine B, ascorbic acid, folic acid, a low-molecular weight dextran, anthranilic acid, porphyrin rings of hemoglobin, alendronate, calcein, erythrosine, and 3-[cyclohexylamino]-1-propanesulfonic acid (CAPS).

4. The method as claimed in claim 3, wherein the duration of step b) ranges from 1 to 15 days following inoculation of the bacteria into the culture medium.

5. The method as claimed in claim 3, wherein said culturing method is a continuous culturing method.

* * * * *